(12) United States Patent
Haider et al.

(10) Patent No.: US 12,738,048 B1
(45) Date of Patent: Sep. 15, 2026

(54) MULTI-AGENT ORCHESTRATED ARTIFICIAL-INTELLIGENCE SYSTEM FOR MEDICAL IMAGING ANALYSIS AND CLINICAL DECISION SUPPORT

(71) Applicant: Lilia AI Inc., Houston, TX (US)

(72) Inventors: Ali Syed Haider, Houston, TX (US); Abdul Muqtadir Khan Durrani, Spring, TX (US); Adam Joseph Watts, Spring Branch, TX (US)

(73) Assignee: LILIA AI INC., Houston, TX (US)

( * ) Notice: Subject to any disclaimer, the term of this patent is extended or adjusted under 35 U.S.C. 154(b) by 0 days.

(21) Appl. No.: 19/419,993

(22) Filed: Dec. 15, 2025

Related U.S. Application Data

(60) Provisional application No. 63/924,210, filed on Nov. 24, 2025.

(51) Int. Cl.
*G06V 10/82* (2022.01)
*G06T 7/00* (2017.01)
(Continued)

(52) U.S. Cl.
CPC ............ *G06V 10/82* (2022.01); *G06T 7/0012* (2013.01); *G06V 10/267* (2022.01); (Continued)

(58) Field of Classification Search
CPC ...... G06V 10/82; G06V 10/86; G06V 10/267; G06V 20/50; G06V 10/993; G06V 10/776;
(Continued)

(56) References Cited

U.S. PATENT DOCUMENTS

| | | | | |
|---|---|---|---|---|
| 12,481,517 | B1 * | 11/2025 | Zhang | G06F 9/45504 |
| 2019/0205606 | A1 * | 7/2019 | Zhou | G06T 7/11 |

(Continued)

OTHER PUBLICATIONS

Tzanis, E., & Klontzas, M. E. (2025). mAIstro: An open-source multi-agent system for automated end-to-end development of radiomics and deep learning models for medical imaging. European Journal of Radiology Artificial Intelligence, 100044. (Year: 2025).*

(Continued)

*Primary Examiner* — Vu Le
*Assistant Examiner* — Jack Peter Kraynak
(74) *Attorney, Agent, or Firm* — Sterne, Kessler, Goldstein & Fox P.L.L.C.

(57) ABSTRACT

Disclosed herein are computer-implemented method, system, and non-transitory computer-readable device aspects for orchestrated multi-agent medical imaging analysis. The disclosed system receives medical imaging data, performs standardized preprocessing, and applies one or more machine-learning inference models to generate intermediate diagnostic outputs. An orchestration agent dynamically selects and invokes specialized downstream agents, including explainability, segmentation, clinical-context fusion, risk scoring, and bias detection agents, based on workflow rules, confidence thresholds, and shared-state memory conditions. The system then generates a structured clinical output comprising diagnostic measurements, visual overlays, narrative explanations, and risk assessments. The multi-agent architecture eliminates fragmented diagnostic pipelines and enables adaptive, reliable, and interpretable clinical decision support. The system further improves robustness by supporting fallback inference, self-healing agent behaviors, and parallel execution paths.

20 Claims, 6 Drawing Sheets

(51) Int. Cl.

| | |
|---|---|
| ***G06V 10/26*** | (2022.01) |
| ***G06V 10/776*** | (2022.01) |
| ***G06V 10/86*** | (2022.01) |
| ***G06V 10/98*** | (2022.01) |
| ***G06V 20/50*** | (2022.01) |
| ***G16H 30/40*** | (2018.01) |

(52) U.S. Cl.
CPC ............ *G06V 10/776* (2022.01); *G06V 10/86* (2022.01); *G06V 10/993* (2022.01); *G06V 20/50* (2022.01); *G16H 30/40* (2018.01); *G06T 2207/20072* (2013.01); *G06T 2207/20081* (2013.01); *G06T 2207/20084* (2013.01); *G06T 2207/30004* (2013.01); *G06V 2201/03* (2022.01)

(58) Field of Classification Search
CPC .... G06V 2201/03; G16H 30/40; G16H 30/00; G16H 30/20; G06T 7/0012; G06T 2207/20072; G06T 2207/20081; G06T 2207/20084; G06T 2207/30004
See application file for complete search history.

(56) References Cited

U.S. PATENT DOCUMENTS

| | | | | |
|---|---|---|---|---|
| 2020/0211692 | A1* | 7/2020 | Kalafut | G16H 50/20 |
| 2020/0303060 | A1* | 9/2020 | Haemel | G16H 40/63 |
| 2023/0334663 | A1* | 10/2023 | Reicher | G16H 30/20 |
| 2025/0166186 | A1* | 5/2025 | Golden | G06T 7/0012 |
| 2025/0349407 | A1* | 11/2025 | Crabtree | A61B 34/30 |
| 2026/0064558 | A1* | 3/2026 | Leonard, II | G06F 11/3438 |

OTHER PUBLICATIONS

Li, S., Xu, J., Bao, T., Liu, Y., Liu, Y., Liu, Y., . . . & Huang, Z. (2025). A co-evolving agentic ai system for medical imaging analysis. arXiv preprint arXiv:2509.20279. (Year: 2025).*

Yu, Yongrui, et al. "Radiologist Copilot: An Agentic Assistant with Orchestrated Tools for Radiology Reporting with Quality Control." arXiv preprint arXiv:2512.02814 (2025). (Year: 2025).*

Slaoui, S. (2025). S-AI: A Sparse Artificial Intelligence System Orchestrated by a Hormonal MetaAgent and Context-Aware Specialized Agents. Int. J. Multidiscip. Res, 7(2). (Year: 2025).*

Roumeliotis, Konstantinos I. et al. "Agentic AI with Orchestrator-Agent Trust: A Modular Visual Classification Framework with Trust-Aware Orchestration and RAG-Based Reasoning." IEEE Access (2025): n. pag. (Year: 2025).*

Williams, K. A., Podgorsak, A. R., Bhurwani, M. M. S., Rava, R. A., Sommer, K. N., & Ionita, C. N. (2021). The Aneurysm Occlusion Assistant, an AI platform for real time surgical guidance of intracranial aneurysms. Proceedings of SPIE—the International Society for Optical Engineering, 11601, 116010V (Year: 2021).*

Ge, Y., Cai, H., Sun, Y et al. An operator-based service orchestration method for medical image intelligent analysis systems. SOCA (2025). https://doi.org/10.1007/s11761-025-00467-6 (Year: 2025).*

Feng, J., Zheng, Q., Wu, C., Zhao, Z., Zhang, Y., Wang, Y., & Xie, W. (Sep. 2025). M 3 builder: A multi-agent system for automated machine learning in medical imaging. In International Workshop on Agentic AI for Medicine (pp. 115-124). Cham: Springer Nature Switzerland. (Year: 2025).*

* cited by examiner

MULTI-AGENT ORCHESTRATED ARTIFICIAL-INTELLIGENCE SYSTEM FOR MEDICAL IMAGING ANALYSIS AND CLINICAL DECISION SUPPORT

CROSS-REFERENCE TO RELATED APPLICATIONS AND INCORPORATION BY REFERENCE

This application claims priority to U.S. Provisional Patent Application No. 63/924,210, filed Nov. 24, 2025, which is incorporated by reference herein in its entirety for all purposes.

TECHNICAL FIELD

The present disclosure relates to computer-implemented systems for medical imaging analysis, and more particularly to orchestrated multi-agent machine-learning architectures for clinical decision support.

BACKGROUND

Conventional medical-AI systems are limited by rigid, monolithic pipelines typically designed around a single modality, such as CT, MRI, ultrasound, ophthalmology OCT, dermatology images, or digital pathology slides, and often operate independently of non-imaging data such as laboratory results, genomic profiles, or electronic-health-record (EHR) metadata. These siloed pipelines cannot incorporate cross-modality evidence, dynamically route data based on intermediate confidence values, or invoke modality-specific analytical processes. As a result, conventional systems frequently reprocess entire datasets unnecessarily, degrade in accuracy when encountering atypical imaging characteristics or missing metadata, and fail to produce holistic clinical assessments.

Existing AI systems also lack unified and context-aware explainability frameworks. Traditional solutions generally offer either a visual heatmap or a text-based explanation, without ensuring consistency between visual evidence and narrative reasoning, or adapting explanation depth based on uncertainty, patient risk, or user role. These isolated post-hoc explanation modules operate independently of the inference pipeline, generating brittle or contradictory outputs that burden clinicians, cannot be validated autonomously, and waste computational resources when detailed explainability is not needed.

Another technical limitation of conventional systems is the absence of unified bias detection or trust-calibration mechanisms spanning multiple modalities and data sources. Existing systems may evaluate fairness for a single model offline, but cannot continuously monitor demographic fairness, scanner variability, slide-scanner heterogeneity, or laboratory-measurement drift in real time. Without integrated disparity-detection and drift-monitoring agents, conventional systems risk silent performance degradation across patient subgroups, requiring costly manual re-evaluation, repeated retraining cycles, and additional computational overhead.

Traditional architectures further fail to incorporate EHR-derived clinical attributes, such as patient history, comorbidities, genetic markers, prior imaging results, or laboratory measurements, into the diagnostic pipeline. As a result, imaging findings must be manually reconciled with patient metadata through separate workflows, causing duplicated queries to clinical systems, increased latency, and an inability to compute personalized risk scores or triage priorities in real time.

Conventional systems also lack operational resilience. When an ML component stalls, receives corrupted inputs, exhausts GPU or memory resources, or produces anomalous outputs, existing pipelines typically fail silently or collapse without automatic recovery. Because conventional systems lack agent-level fault detection, fallback model invocation, or dynamic rerouting, a single failure or low-confidence component forces a manual pipeline restart, wasting compute cycles, delaying care, and compromising reliability in time-sensitive environments.

Conventional medical-AI architectures additionally lack integrated support for model lifecycle operations, including safe deployment of updated models, regression testing, clinical simulation, or institutionalized federated learning. Traditional systems rely on manual scripts or offline evaluation to validate new models, which increases latency, introduces versioning risk, and requires redundant computational infrastructure. Without a simulation agent, governance agent, or self-healing agent, conventional platforms cannot safely evaluate new model behaviors, track lineage, or support privacy-preserving training based on institution-specific patient populations.

Conventional clinical-trial-matching and drug-response-prediction systems similarly operate in isolation from imaging and diagnostic AI pipelines. Existing matching systems generally rely on manual EHR queries or static rule-based systems that do not incorporate imaging-derived features, pathology findings, or genomic signatures. Existing drug-response models are typically trained using narrow datasets without dynamic integration of radiologic features, cellular morphology, biomarker patterns, and structured EHR data, resulting in limited predictive accuracy and operational inefficiency.

Accordingly, improved technological solutions are needed to address these deficiencies and provide a unified, adaptive medical-AI architecture capable of coordinating multimodal analysis, context-aware explainability, continuous bias and drift monitoring, clinical-attribute fusion, and resilient system-level recovery directly within the inference pipeline. Such technological advancements would enable more reliable, efficient, and contextually informed clinical decision support without the redundant processing, manual reconciliation, version-control risk, or operational fragility that characterize conventional systems.

BRIEF DESCRIPTION OF THE DRAWINGS

The accompanying drawings are incorporated herein and form a part of the specification.

In the drawings, like reference numbers generally indicate identical or similar elements. Additionally, generally, the left-most digit(s) of a reference number identifies the drawing in which the reference number first appears.

DETAILED DESCRIPTION

Figure 1:
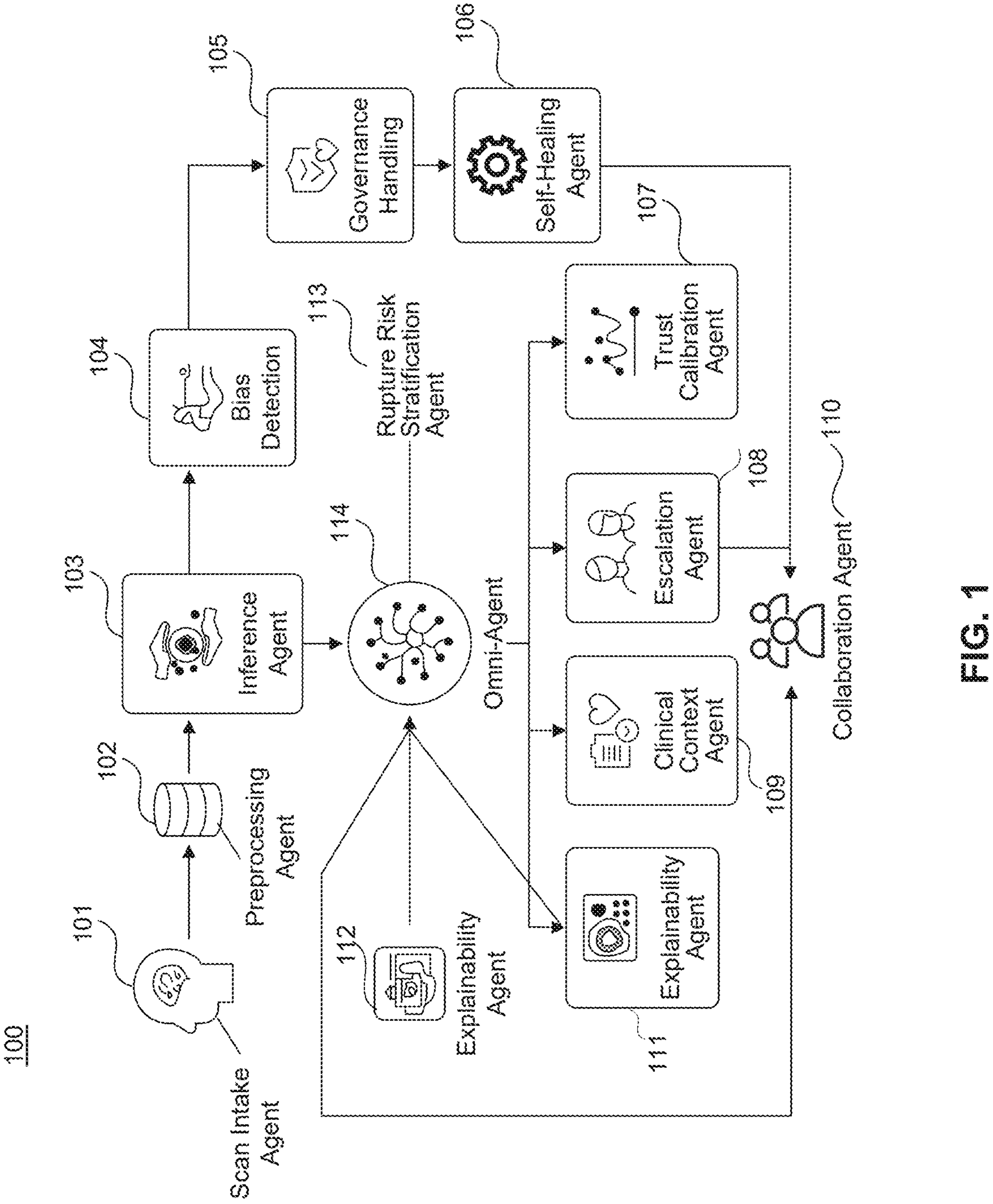
FIG. 1 illustrates an example block diagram of a multi-agent medical imaging analysis architecture, according to some aspects. The diagram depicts the major components of the system, including a scan intake agent, a preprocessing agent, an inference agent, a shared-state memory structure, an orchestration agent, and a plurality of downstream specialized agents that contribute to clinical output generation.

According to embodiments, the disclosed system addresses the limitations of conventional medical-AI pipelines through a dynamic, multi-agent architecture coordinated by a centralized orchestration agent ("omni-agent"). The omni-agent evaluates model-confidence scores, modality identifiers, metadata completeness, computational resource availability, and clinical-priority attributes to route data among specialized agents. These agents may include inference, segmentation, classification, explainability, clinical-context fusion, clinical-trial analysis, drug-response modeling, bias detection, self-healing, simulation, and governance agents. This coordinated execution allows the system to invoke only the agents required for a particular workflow, select fallback or modality-specific models when outputs are ambiguous, continuously monitor fairness and drift, and fuse multimodal data into coherent diagnostic assessments.

In certain embodiments, the system supports dual-mode explainability through activation maps, saliency overlays, stain-normalized pathology representations, and natural-language rationales, each validated using trust-calibration and consistency-checking metrics. A clinical-trial matching agent may parse inclusion and exclusion criteria using natural-language processing and compare those criteria to multimodal patient representations derived from imaging, pathology, genomics, and EHR data. A drug-response modeling agent may predict therapeutic effect or treatment suitability using machine-learning models trained on large multimodal datasets. Additional agents, including a self-healing agent and a governance agent, may detect faulty outputs, restore corrupted states, reroute workflows to fallback models, maintain model lineage, manage audit trails, and track regulatory metadata.

According to embodiments, these techniques provide concrete technological improvements over traditional monolithic pipelines. Context-adaptive agent invocation reduces unnecessary computation, multimodal fusion enhances predictive accuracy, and trust-validated explainability improves safety and interpretability. Integrated bias monitoring, clinical-trial assessment, drug-response prediction, and self-healing replace redundant downstream systems while improving reliability, regulatory readiness, and clinical preparedness.

In addition, the disclosed techniques improve the functioning of a computing system itself. By orchestrating distributed agents rather than executing rigid, fixed-sequence pipelines, the system more efficiently allocates CPU, GPU, and memory resources, reduces full-pipeline re-execution after component failures, and minimizes bandwidth usage in federated-learning configurations by avoiding transfer of raw clinical data. Integrated simulation-based regression testing, dynamic interpretability validation, and drift monitoring further simplify safe model deployment and reduce infrastructure overhead across hospital networks, telemedicine systems, cloud-based AI environments, resource-limited clinical settings, and multi-institutional research deployments.

According to embodiments, the backend architecture may be implemented as a distributed, containerized computational platform supporting high-throughput medical-imaging analysis and multi-agent orchestration. The architecture may include a preprocessing engine that performs skull stripping, intensity normalization, slice-consistency verification, and metadata harmonization. The preprocessing engine may use GPU-accelerated voxel-processing pipelines and noise-reduction routines suitable for CT, CTA, or MRI datasets. Prior to downstream analysis, the preprocessing engine may validate anatomical coverage, correct gantry-tilt metadata, and adjust voxel intensities using modality-specific reference distributions to ensure that subsequent models receive harmonized and artifact-resistant inputs.

In some embodiments, the architecture includes model-execution containers configured to run deep-learning models stored in H5, PTH, ONNX, or other formats. These containers may support frameworks such as TensorFlow, PyTorch, and ONNX Runtime, each isolated within a lightweight virtualization layer and exposing a standardized tensor interface to the orchestration layer. Containers may incorporate dedicated GPU kernels, fused-operator libraries, and model-graph optimization routines that prune or recompile models during execution to improve runtime performance and maintain compatibility across disparate modeling environments.

According to embodiments, the orchestration layer coordinates thirteen specialized agents in a dependency-aware manner using workflow-graph structures, shared-state memory objects, and telemetry-based routing decisions. Agents may include intake, preprocessing, classification, segmentation, sizing, risk assessment, explainability, clinical context, bias detection, escalation, billing, clinical-trial assessment, and summary generation. In some implementations, the unified controller supports dynamic graph rewiring that allows newly added models or institution-specific modules to be incorporated without architectural redesign.

In certain embodiments, data storage is provided by a secure imaging repository compliant with HIPAA and other privacy regulations. The repository may maintain encrypted volumes, audit logs, DICOM gateways, and immutable write-ahead logs capturing lineage for each execution. Stored items may include raw images, processed volumes, segmentation masks, measurement vectors, explainability visualizations, risk scores, fairness metrics, and billing artifacts. A tiered storage structure spanning device memory, host RAM, and SSD storage may be used to minimize latency and expedite access to frequently utilized tensors.

According to embodiments, the system may include an explainability and visualization engine configured to render heatmaps, saliency overlays, textual explanations, and three-dimensional attribution volumes. These outputs may incorporate segmentation contours, measurement annotations, and multimodal overlays integrating CT, MRI, EHR-derived features, and guideline references. An API layer may expose these results to clinical interfaces while supporting secure request handling and parallel inference. Optional EMR or PACS integration may be provided through FHIR, HL7, or DICOMweb interfaces.

The architecture may also incorporate a clinical-reasoning agent configured to apply medical rulesets, guideline-compliant frameworks, and structured scoring algorithms to interpret agent outputs. These rulesets may reflect treatment guidelines, contraindication rules, clinical-trial criteria, or institution-specific workflows. A bias-detection layer may monitor scanner variability, perform demographic-stratified error analysis, and compute fairness metrics to ensure equitable model performance across patient groups.

In some embodiments, a report-generation engine aggregates outputs from all agents into a clinician-ready summary containing segmentation views, morphological measurements, risk estimates, guideline citations, explainability artifacts, fairness analyses, and billing codes. The engine may apply templating logic, anatomical labeling, and consistency checking before final output.

According to embodiments, system operation begins when a medical scan is uploaded to an API or graphical interface. The intake agent validates the scan, extracts DICOM metadata, confirms orientation, identifies modality, and evaluates image quality. The preprocessing agent then performs normalization, skull stripping, contrast enhancement, and tensor preparation for model execution. The classification agent determines whether the scan contains evidence of aneurysm, stroke, or another supported abnormality. Upon detection, the segmentation agent delineates lesion boundaries and the sizing agent computes volumetric and geometric measurements. These outputs are then evaluated by the risk-assessment agent to produce rupture-risk estimates, NIHSS severity scores, or other clinical indices. The explainability agent produces visual and textual rationales that illustrate how model outputs were derived.

According to embodiments, the clinical-context agent integrates imaging findings with guideline-based recommendations and patient metadata. The bias-detection agent evaluates fairness metrics and demographic performance consistency. High-risk cases may trigger alerts through the escalation agent. Billing codes may be produced by the billing agent, and the clinical-trial agent may evaluate eligibility for active studies. The summary agent consolidates all results into a unified report for clinician review.

According to embodiments, the system may operate in conjunction with CT scanners, CTA systems, MRI scanners, ultrasound devices, or PACS archives. Processing may be performed on servers equipped with CPU and GPU compute resources or on cloud-based infrastructures. Clinicians may access the system through browsers, desktop applications, or mobile interfaces communicating with a backend API. Deployments may span cloud, hybrid, or edge environments, with optional EMR integration via HL7, FHIR, or proprietary messaging systems.

In some embodiments, enhancements may include MRI-specific preprocessing pipelines, multi-disease detection capabilities, real-time inference streamed directly from scanners, on-device inference for portable platforms, multi-agent consensus scoring from diverse model architectures, workflow-engine integrations for hospital systems, and reinforcement-learning-based segmentation refinement.

FIG. 1 is a block diagram illustrating a multi-agent medical imaging analysis system 100 for orchestrated clinical decision support, according to some embodiments. System 100 may represent a comprehensive artificial intelligence architecture that can coordinate multiple specialized agents to perform end-to-end medical imaging analysis, from initial data ingestion through final clinical output generation. The system may address critical limitations in conventional medical AI by implementing a dynamic, agent-based approach that can enable selective execution, fault tolerance, and multimodal data integration.

System 100 may include scan intake agent 101, preprocessing agent 102, inference agent 103, omni-agent 114, explainability agent 111, clinical context agent 109, escalation agent 108, trust calibration agent 107, self-healing agent 106, governance agent 105, bias detection agent 104, rupture risk stratification agent 113, and collaboration agent 110. Each agent may represent a specialized component designed to perform specific functions within the overall diagnostic workflow, while omni-agent 103 may serve as the central orchestration engine that can coordinate agent execution based on confidence scores, workflow rules, and system state.

Scan intake agent 101 may serve as the entry point for medical imaging data into system 100. Scan intake agent 101 may be configured to receive and validate various types of medical imaging data, which may include DICOM images from CT scanners, MRI systems, ultrasound devices, digital pathology slides, dermatology images, ophthalmology scans, or other medical imaging modalities. In some embodiments, scan intake agent 100 may validate imaging format integrity, scanner-model identifiers, acquisition protocols, slice completeness, modality specifications, and anonymization status to ensure HIPAA compliance. For example, when processing brain aneurysm detection workflows, scan intake agent 101 may specifically validate NIfTI file formats, extract DICOM metadata including patient demographics, scan parameters, and acquisition timestamps, and perform initial quality assessments to determine whether the imaging data meets minimum standards for downstream processing.

Scan intake agent 101 may also classify incoming studies by urgency level, imaging modality, and clinical indication. For instance, in emergency scenarios involving suspected stroke or aneurysm rupture, scan intake agent 101 may automatically flag studies for expedited processing and trigger immediate notification pathways. The agent may maintain compatibility with hospital PACS systems, enabling seamless integration with existing radiology workflows. In some embodiments, scan intake agent 101 may support batch processing of multiple studies while maintaining individual case tracking and provenance records.

Preprocessing agent 102 may receive validated imaging data from scan intake agent 100 and perform comprehensive data preparation operations. Preprocessing agent 102 may execute both deterministic and machine-learning-based transformations to standardize imaging data for downstream analysis. These operations may include skull stripping for brain imaging studies, noise reduction using convolutional filters, voxel-intensity normalization, resampling to standardized voxel grids, orientation alignment, artifact detection and removal, and computation of quality metrics such as signal-to-noise ratios, slice-continuity scores, and artifact-presence scores.

In brain aneurysm detection embodiments, preprocessing agent 102 may perform specialized operations including brain extraction to remove non-brain tissue, intensity normalization to account for scanner variations, and resampling to ensure consistent spatial resolution across different acquisition protocols. Preprocessing agent 102 may also apply advanced denoising algorithms specifically tuned for neurovascular imaging, enhancing the visibility of small vascular structures while preserving critical anatomical details. Preprocessing agent 102 may generate quality assessment reports that can influence downstream agent selection and processing parameters.

Inference agent 103 may comprise one or more trained neural network models configured to perform core diagnostic analysis on preprocessed imaging data. Inference agent 103 may implement various deep learning architectures including U-Net models for segmentation tasks, three-dimensional convolutional neural networks for volumetric analysis, transformer models for attention-based feature extraction, or hybrid architectures that combine multiple approaches. The agent may be configured to output segmentation masks, bounding volumes, surface meshes, probability scores, and confidence values associated with detected abnormalities. In aneurysm detection applications, inference agent 103 may utilize specialized models trained on expert-annotated datasets to identify vascular abnormalities, classify aneurysm types (saccular, fusiform, dissecting), determine anatomical locations (middle cerebral artery, internal carotid artery, basilar artery), and compute morphological measurements including height, neck width, dome-to-neck ratios, and volumetric assessments. The agent may implement cascaded neural networks that separately perform detection and segmentation tasks, enabling more accurate localization and characterization of identified lesions. Inference agent 103 may also support multi-framework execution, simultaneously running TensorFlow H5 models and PyTorch PTH models within the same workflow. This capability may enable the system to leverage the best-performing models regardless of their implementation framework. The agent may generate three-dimensional reconstructions of anatomical structures, providing detailed visualizations for clinical review and measurement validation.

Omni-agent 114 may function as the central orchestration engine that manages and synchronizes the operation of all specialized agents within system 100. In some embodiments, omni-agent 114 may receive intermediate or final inference outputs from inference agent 103 and determine subsequent processing steps using confidence thresholds, workflow-graph traversal logic, rule-based decisioning, or machine-learned routing policies. The omni-agent may also maintain a shared-state memory structure containing tensors, metadata attributes, provenance markers, timestamps, uncertainty scores, and workflow-state indicators, allowing distributed agents to make consistent, context-aware decisions throughout the processing pipeline.

Omni-agent 114 may implement a graph-based state machine that defines permissible agent transitions and corresponding conditions. For example, if inference agent 103 produces low-confidence segmentation results, omni-agent 114 may automatically re-invoke the inference process using alternative neural networks with distinct architectures or training data. The agent may also trigger parallel execution of multiple specialized agents when workflow conditions warrant comprehensive analysis, or sequential execution when computational resources are constrained.

In some embodiments, omni-agent 114 may incorporate predictive anomaly-detection capabilities trained to identify early indicators of workflow instability or impending component failures. These capabilities may include monitoring of inter-agent communication latencies, tensor-shape irregularities, abnormal gradients, configuration drift, and deviations from historical execution patterns. By forecasting potential failures before components become unresponsive, the omni-agent can initiate proactive interventions such as pre-emptive rerouting, graceful degradation, or warm-start reinitialization of specific agents. Omni-agent 114 may further detect deadlocks, stalls, or partial hangs through latency thresholds, heartbeat-monitoring signals, and dependency-graph timeouts, automatically invoking recovery routines, fallback neural networks, or alternative analytic pathways to maintain continuous operation. In some implementations, omni-agent 114 may also manage federated-learning model updates across multiple institutions, coordinating secure aggregation of model deltas, enforcing privacy-preserving protocols, validating model lineage, and deploying updated inference components without interrupting ongoing clinical workflows. This continuous-learning capability enables the system to improve performance over time while maintaining compliance with institutional data-governance and privacy requirements.

Bias detection agent 104 may address critical fairness, robustness, and equity concerns in medical-AI deployments by continuously monitoring system performance across demographic groups, imaging devices, data modalities, and acquisition conditions. In some embodiments, the agent may compute scanner-derived and demographic-derived fairness metrics using statistical techniques such as chi-square testing, Kolmogorov-Smirnov testing, demographic-stratified error analysis, confidence-interval comparison, and KL-divergence-based distribution-shift measurements. Bias detection agent 104 may maintain rolling performance baselines for subgroups defined by age ranges, gender categories, ethnic populations, clinical-history cohorts, scanner manufacturers, reconstruction kernels, firmware versions, or acquisition protocols, enabling detection of both gradual drift and abrupt deviations. The agent may further evaluate internal model signals, such as embedding-space distributions, intermediate feature activations, attention-weight patterns, and calibration-curve divergence, to identify structural sources of bias within the underlying neural networks.

In some implementations, bias detection agent 104 may incorporate multimodal attribution analysis to determine whether observed disparities arise from imaging features, EHR-derived clinical attributes, genomic markers, laboratory measurements, or cross-modality interactions. The agent may also employ online drift-detection algorithms including CUSUM, ADWIN, and Page-Hinkley tests to identify emerging fairness issues in streaming or batched inference workloads. To provide deeper analysis, the agent may perform counterfactual fairness simulations by substituting or masking demographic variables while preserving clinical features to determine whether model outputs remain stable under counterfactual demographic conditions. When performance disparities exceed predefined thresholds, bias detection agent 104 may automatically notify omni-agent 103 and trigger remediation workflows such as subgroup-specific threshold calibration, sample-reweighting procedures, adversarial debiasing routines, domain-adaptation pipelines, or targeted fine-tuning using institution-specific datasets. In federated or distributed environments, the agent may coordinate fairness evaluation across remote clinical sites by securely aggregating subgroup-specific metrics without transferring raw patient data. This continuous, multi-layered monitoring framework enables real-time detection and mitigation of fairness issues across modalities, scanners, and clinical populations, thereby improving the resilience and trustworthiness of system 100. For example, in aneurysm detection workflows, bias detection agent 104 may monitor whether the system exhibits differential performance for elderly patients versus younger populations, or whether certain scanner manufacturers' equipment produces systematically different results. The agent may generate alerts when fairness metrics exceed predefined thresholds, triggering model retraining or calibration procedures. Bias detection agent 104 may also maintain longitudinal tracking of fairness metrics, enabling identification of performance drift over time and across different patient populations.

Governance agent 105 may ensure regulatory compliance, audit trail maintenance, and model lineage tracking throughout the diagnostic workflow. Governance agent 105 may maintain comprehensive records of all agent executions, model versions, input data characteristics, intermediate results, and final outputs. The agent may generate reports formatted for FDA submissions, IRB reviews, and hospital quality assurance programs. In some embodiments, governance agent 105 may implement differential privacy mechanisms for model updating operations and secure aggregation of institution-level model updates.

Governance agent 105 may also track consent management, ensuring that patient data usage complies with institutional policies and regulatory requirements. Governance agent 105 may maintain version control for all system components, enabling rollback capabilities and reproducible analysis workflows. The agent may generate provenance metadata that documents the complete processing history for each case, supporting clinical decision-making and legal requirements.

Self-healing agent 106 may provide operational resilience by detecting and responding to system failures, component malfunctions, and performance degradations. Self-healing agent 106 may monitor all system components for signs of failure including excessive processing times, memory exhaustion, GPU resource conflicts, or anomalous output patterns. When failures are detected, the agent may automatically restart failed components, reroute processing to alternative computational resources, or invoke backup processing pathways.

In some embodiments, self-healing agent 106 may implement predictive failure detection using machine learning models trained on historical system performance data. The agent may identify patterns that precede system failures, enabling proactive intervention before critical components become unavailable. Self-healing agent 106 may also coordinate with external DevOps systems, logging incidents and triggering automated recovery procedures that extend beyond the immediate medical imaging workflow.

Trust calibration agent 107 may manage confidence assessment and uncertainty quantification across all system components. Trust calibration agent 107 may monitor model confidence scores, compare predictions against ground-truth labels when available, and maintain calibration curves that ensure confidence scores accurately reflect prediction reliability. The agent may adjust confidence thresholds dynamically based on system performance history and clinical requirements. For example, in emergency scenarios requiring high sensitivity, trust calibration agent 107 may lower confidence thresholds to ensure that potential abnormalities are not missed, while in screening scenarios where specificity is prioritized, the agent may raise thresholds to reduce false positive rates. The agent may also implement ensemble methods that combine predictions from multiple models to improve overall reliability and uncertainty estimation.

Escalation agent 108 may manage clinical alert generation and communication with healthcare providers based on risk assessments and urgency determinations. Escalation agent 108 may implement tiered triage systems that classify findings as urgent, semi-urgent, or routine based on clinical severity and patient risk factors. The agent may integrate with hospital communication systems including paging networks, electronic health record systems, and mobile notification platforms. In aneurysm detection workflows, escalation agent 108 may automatically generate immediate alerts for large aneurysms with high rupture risk, while routing smaller, stable lesions through standard reporting channels. The agent may support FHIR-compliant messaging interfaces, enabling seamless integration with diverse healthcare IT infrastructures. Escalation agent 108 may also maintain communication logs and response tracking to ensure that critical findings receive appropriate clinical attention.

Clinical context agent 109 may integrate imaging-derived findings with electronic health record data, patient history, laboratory results, and other clinical information to provide comprehensive diagnostic assessments. Clinical context agent 109 may access structured EHR data including demographics, comorbidities, medication lists, prior imaging studies, and laboratory values to contextualize current findings within the patient's overall clinical picture. For example, when analyzing aneurysm detection results, clinical context agent 109 may incorporate patient age, hypertension history, family history of cerebrovascular disease, and prior imaging studies to compute personalized risk assessments. The agent may apply clinical decision rules, evidence-based guidelines, and machine learning models trained on multimodal datasets to generate patient-specific recommendations for follow-up care, treatment planning, and monitoring strategies.

Collaboration agent 110 may facilitate multi-user interaction and decision-making support for complex cases requiring specialist consultation. Collaboration agent 110 may provide real-time synchronized annotation capabilities, enabling radiologists, neurologists, neurosurgeons, and other specialists to collaboratively review cases and document their findings. The agent may maintain discussion logs, decision rationales, and consensus tracking to support quality assurance and educational activities. In some embodiments, collaboration agent 110 may implement role-based access controls, ensuring that different user types have appropriate permissions for viewing, annotating, and modifying case information. The agent may also support asynchronous collaboration, enabling specialists in different time zones or schedules to contribute to case reviews and decision-making processes.

Explainability agent 111 may generate comprehensive explanations for AI-driven diagnostic decisions, combining visual and textual modalities to support clinical understanding and trust. Explainability agent 111 may produce Grad-CAM overlays that highlight image regions most influential in diagnostic decisions, attention-based visual overlays that show model focus areas, and natural-language explanations generated using large language models trained on medical literature and clinical reasoning patterns. Explainability agent 111 may implement explainability fusion techniques that quantify agreement between visual attention maps and textual explanations, ensuring consistency between different explanation modalities. Explainability agent 111 may also validate semantic statements against segmentation outputs using consistency analysis, preventing contradictory or misleading explanations. In aneurysm detection applications, the agent may generate explanations that describe aneurysm location, morphological characteristics, size measurements, and risk factors in clinically appropriate language.

Rupture risk stratification agent 113 may compute specialized risk assessments for vascular abnormalities using established clinical scoring systems and advanced predictive models. Rupture risk stratification agent 113 may implement PHASES (Population, Hypertension, Age, Size, Earlier SAH, Site) scoring, UJATS (Unruptured Intracranial Aneurysm Treatment Score) assessment, or hybrid models that combine traditional risk factors with imaging-derived features and machine learning predictions. Rupture risk stratification agent 113 may incorporate morphological measurements from inference agent 102, patient demographics and clinical history from clinical context agent 109, and imaging characteristics to generate comprehensive rupture risk assessments. Rupture risk stratification agent 113 may provide both absolute risk estimates and relative risk comparisons, enabling clinicians to make informed decisions about treatment timing, monitoring intervals, and intervention strategies.

In an alternative embodiment, system 100 may be implemented as a distributed, cloud-native platform that supports multi-institutional deployment, federated learning, and cross-site orchestration. In such configurations, individual healthcare institutions may deploy local, on-premises instances of system 100, each containing a subset or full complement of specialized agents, while participating in collaborative model-improvement workflows that do not require sharing raw patient data. Federated-learning operations may be coordinated by omni-agent 114 or a dedicated federated-update agent configured to distribute global model parameters, collect encrypted model deltas, and perform secure aggregation using protocols such as secure multiparty computation, homomorphic encryption, or trusted execution environments. Differential privacy mechanisms may be applied to gradient updates or weight vectors to prevent reconstruction of patient-specific information. The distributed architecture may further allow institutions, vendors, or research partners to contribute new agents into an extensible agent registry, enabling a plug-and-play ecosystem in which interoperable AI components, developed independently but conforming to a shared communication and state-management interface, can be dynamically incorporated to address diverse clinical tasks.

This alternative embodiment may also support hybrid edge-cloud computing deployments in which agents are divided between local and remote execution environments based on latency, reliability, and resource constraints. For example, latency-critical agents such as scan intake agent 101, preprocessing agent 102, inference agent 103, and routing components by omni-agent 114 may operate on local hardware, including GPU-enabled edge servers or embedded devices located within radiology suites. This allows imaging studies to be processed even when wide-area network connectivity is degraded or unavailable. Meanwhile, non-time-critical agents, such as bias detection agent 104, governance agent 105, audit agent 109, and collaboration agent 110, may execute in cloud or regional datacenter environments that provide scalable compute, long-term storage, advanced simulation tools, and compliance-support infrastructure. Synchronization between edge and cloud components may be achieved through asynchronous message queues, versioned state objects, and conflict-resolution policies that ensure consistent model behavior across distributed environments. In some embodiments, the system may automatically transition between edge-only, cloud-only, or hybrid execution modes based on network health, workload distribution, or institutional preference.

The system may further be extended to support additional imaging modalities, non-imaging data sources, and clinical applications beyond aneurysm detection. These applications may include oncologic lesion screening across CT, PET, MRI, and digital pathology; cardiac functional analysis and myocardial quantification; musculoskeletal injury assessment; neurodegenerative-disease progression modeling; ophthalmic OCT analysis; and rare-disease detection using multimodal feature fusion. Each domain may deploy specialized versions of the core agents, such as modality-specific preprocessing pipelines, model-architecture selectors, genomic-integration modules, or domain-adaptation subagents, while maintaining compatibility with the orchestration logic, shared-state memory structures, and routing policies managed by omni-agent 114. This modular and extensible design enables system 100 to evolve across new modalities and clinical workflows without architectural rewrites, allowing the platform to serve as a unified operational layer for next-generation medical-AI ecosystems.

Figure 2:
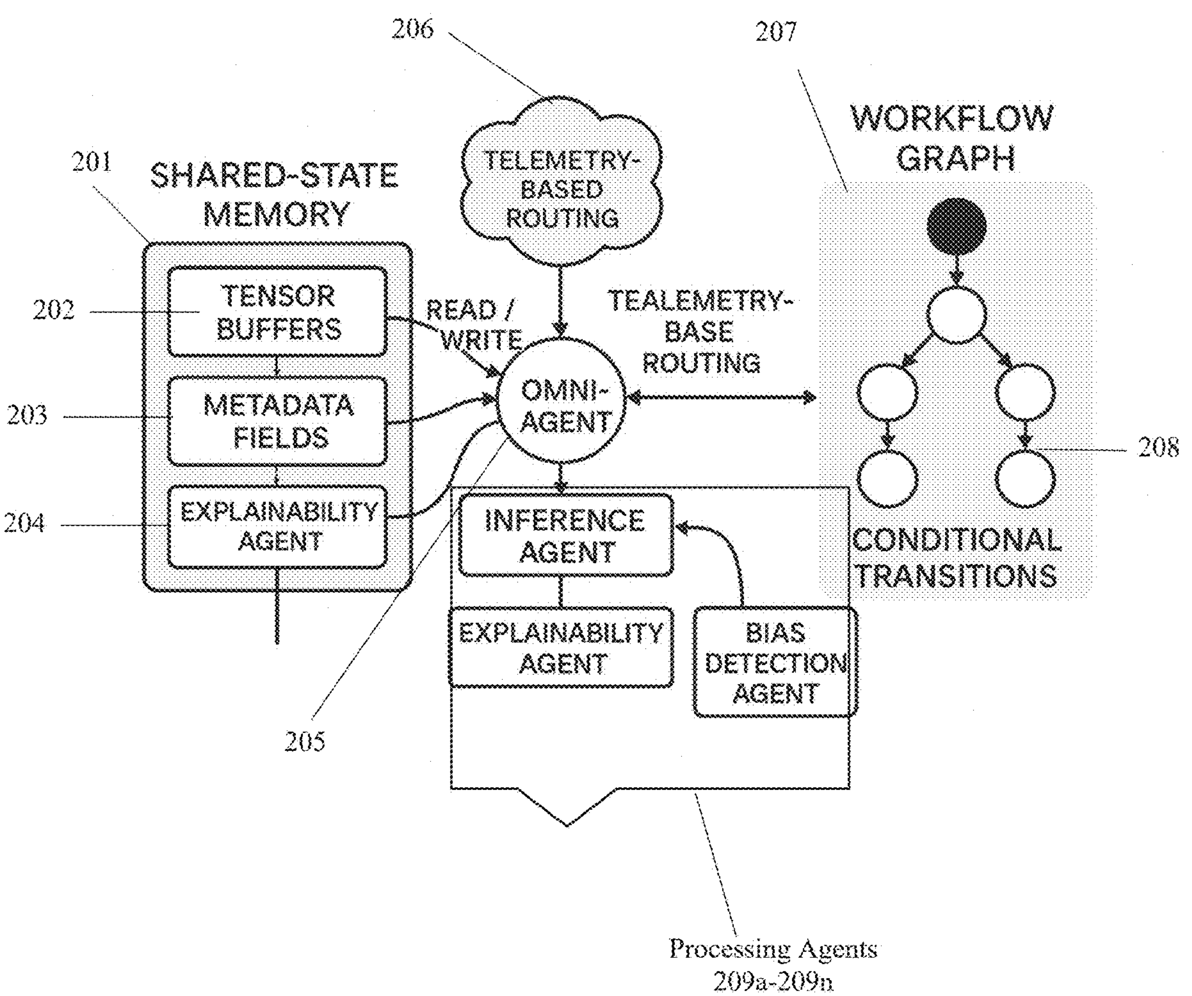
FIG. 2 illustrates an example flow diagram for orchestrating specialized agent execution based on workflow rules and confidence thresholds.

FIG. 2 illustrates an exemplary architecture 200 for orchestrating data flow among multiple machine-learning agents using a shared-state memory model and a workflow-graph routing framework. As shown, a shared-state memory module 201 provides a centralized data structure accessible to multiple components of the system. The shared-state memory module 201 may include one or more tensor buffer structures 202 configured to store intermediate activation maps, segmentation volumes, attribution tensors, or other multidimensional numerical arrays produced by downstream agents. Shared-state memory module module 201 may further include metadata fields 203 that store patient identifiers, imaging-protocol descriptors, acquisition parameters, model-confidence values, historical inference outputs, or other contextual information necessary for coordinated agent operation. In certain embodiments, the shared-state memory module 201 may additionally store explainability-related artifacts generated by an explainability-agent interface 204, enabling subsequent agents to retrieve attribution signals without recomputation.

The system may include an omni-agent 205, implemented as the central orchestration engine responsible for coordinating read and write operations with the shared-state memory module 201. Omni-agent 205 may perform memory-managed access operations to tensor buffers 202 and metadata fields 203, using deterministic or priority-weighted scheduling algorithms to maintain consistency between upstream and downstream agents. In one embodiment, omni-agent 205 evaluates telemetry obtained from a telemetry-based routing module 206, which tracks GPU utilization, inference-time variance, memory fragmentation, and operational health metrics of individual agents. Telemetry-based routing module 206 may supply omni-agent 205 with real-time operational indicators allowing dynamic adjustments to agent execution order or selection of fallback computational paths.

Omni-agent 205 may also interact with a workflow graph 207, which encodes clinical, computational, and dependency-based rules governing agent transitions. The workflow graph 207 may define a plurality of conditional transitions 208, each specifying conditions under which execution progresses to a particular downstream agent. Conditional transitions 208 may be dependent on confidence thresholds, modality identifiers, metadata completeness, or inter-agent consistency metrics. In some embodiments, workflow graph 207 may be dynamically rewired during runtime based on telemetry signals or newly ingested metadata, enabling adaptive execution paths that reflect patient-specific or resource-specific considerations.

Based on telemetry, workflow-graph rules, and monitored outputs stored within shared-state memory 201, omni-agent 205 may direct data to one or more specialized processing agents 209*a*-209*n*. As represented in FIG. 2, the system may, for example, include an inference agent, an explainability agent, and a bias-detection agent, among other agents. The inference agent may perform core model execution such as lesion detection or volumetric segmentation. The explainability agent 210 may compute saliency maps, feature-importance contours, or textual rationales. The bias-detection agent 211 may compute subgroup-fairness metrics, scanner-variability indicators, or demographic-stratified error rates. Each agent may read from and write to shared-state memory module 201 and may be invoked, skipped, or replaced depending on the routing decisions performed by omni-agent 205.

The architecture shown in FIG. 2 demonstrates how the disclosed system departs from traditional monolithic inference pipelines by enabling dynamic, context-aware, and telemetry-driven agent orchestration. By coordinating access to shared-state memory 201 and enforcing workflow-graph transitions 207, omni-agent 205 supports conditional execution pathways, real-time fallback logic, and adaptive multi-agent collaboration. These technical features improve computational efficiency, system reliability, and diagnostic consistency across varying imaging modalities, resource conditions, and patient-specific clinical scenarios.

Figure 3:
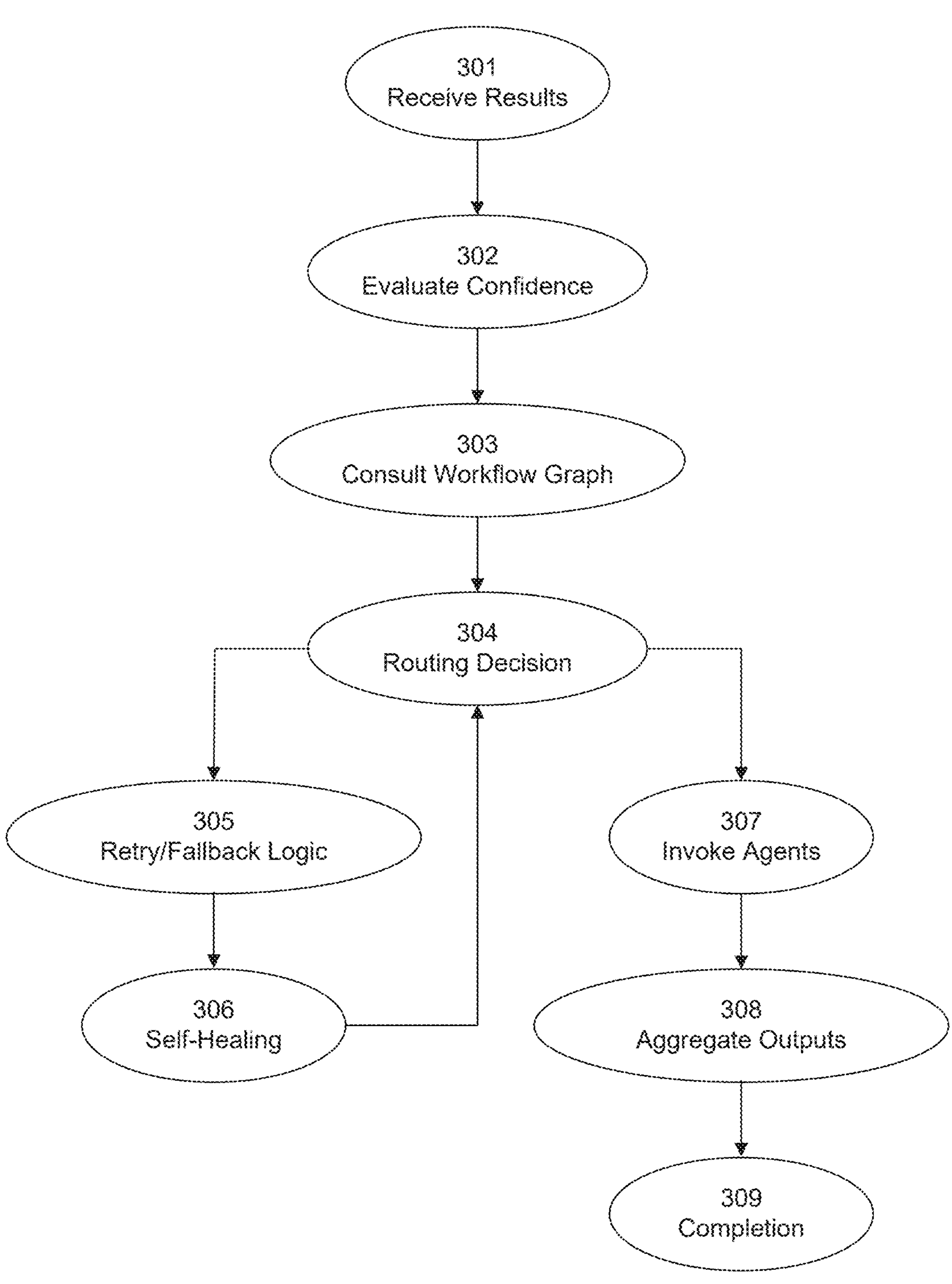
FIG. 3 illustrates an example block diagram of an orchestration-driven workflow for agent selection and output synthesis, according to some aspects.

FIG. 3 illustrates an exemplary routing and orchestration workflow executed by omni-agent 103 for coordinating processing across the specialized agents within system 100. Figure X illustrates an exemplary routing and orchestration workflow executed by omni-agent 103 for dynamically coordinating processing across the specialized agents of system 100. The workflow begins at step 301, where omni-agent 103 receives outputs generated by inference agent 102 or other upstream agents. These outputs may include one or more tensors, segmentation masks, classification vectors, reconstruction maps, metadata values, uncertainty indicators, and provenance records. In some embodiments, these outputs may be stored directly in a shared-state memory object that is implemented using pinned host memory regions, device buffers, zero-copy serialization buffers, or direct-mapped key-value stores. This structure allows GPU kernels associated with inference agent 102 to write results directly into shared memory locations that downstream agents can access without redundant copying or re-encoding, thereby reducing latency and improving computational efficiency. Incoming data may also be timestamped, versioned, and optionally cryptographically signed to preserve lineage across distributed or federated deployments.

At step 302, omni-agent 103 evaluates the confidence associated with the received outputs. Confidence may be computed using predictive entropy, mutual-information estimates, softmax calibration curves, or uncertainty scores derived from Monte Carlo dropout, deep ensembles, or other uncertainty-estimation methods. Confidence evaluation may also incorporate metadata, such as scanner noise metrics, protocol adherence indicators, slice completeness scores, laboratory data quality indicators, or EHR consistency checks. In some embodiments, omni-agent 103 may rely on a confidence prediction model trained to detect unreliable results based on tensor statistics, imaging artifacts, prior patient history, or cross-modality inconsistencies. The evaluation process may further include tensor-shape validation, boundary-condition checks, and inspection of abnormal activations or gradient magnitudes that may indicate corrupted inputs or model instability. This combination of statistical and structural assessment ensures that routing decisions are informed by a robust, multi-factor reliability score.

At step 303, omni-agent 103 consults a workflow graph that encodes permissible processing paths, dependencies, and conditional transitions among agents. The workflow graph may be implemented as a directed acyclic graph, a finite-state machine, or a dynamically learned policy graph. Each node corresponds to an agent, while each edge defines a condition, rule, or confidence threshold that governs whether execution may transition to the next agent. The workflow graph may be stored in a graph database, rule engine, or decision-policy model, and may be updated at runtime to accommodate new agents, new clinical workflows, or new facility-specific routing policies. System 100 may further maintain metadata describing each node's computational cost, memory footprint, latency constraints, and compatibility with device resources. In some embodiments, the workflow graph may have separate subgraphs for edge devices, cloud environments, and federated nodes to support hybrid execution strategies.

At step 304, omni-agent 103 generates a routing decision by combining the results of the confidence evaluation, the workflow graph, system telemetry, and the contents of the shared-state memory object. System telemetry may include GPU utilization, queue depth, kernel launch latency, memory fragmentation, CPU scheduling load, I/O wait time, and network health. Telemetry may be sampled continuously at millisecond or sub-millisecond intervals. Omni-agent 103 may incorporate telemetry directly into routing decisions to avoid conditions such as GPU oversubscription, excessive memory thrashing, or unbalanced load across heterogeneous compute devices. Routing decisions may rely on rule-based decision trees, heuristic policies, or reinforcement-learning agents trained to maximize throughput, minimize latency, or optimize reliability for specific imaging modalities or patient populations. The routing decision identifies whether to continue normal processing, retry processing, or initiate a self-healing routine.

If omni-agent 103 determines that the incoming results are unreliable or inconsistent with expected behavior, the agent may initiate retry and fallback logic at step 305. During this stage, the system may re-run inference using alternative neural networks implemented using different architectures, training data distributions, or robustness optimizations. Some fallback networks may be pruned or quantized versions of primary models to reduce computational requirements, enabling fast recovery on resource-constrained edge devices. Retry logic may also involve applying localized preprocessing operations such as region-of-interest extraction, de-noising, artifact suppression, missing-slice interpolation, or scanner-specific correction models. In some embodiments, omni-agent 103 may analyze low-level indicators such as tensor-shape mismatches, CUDA kernel exit codes, or abnormal gradient values to determine whether a computational failure occurred. These fallback mechanisms provide structured resilience and prevent unnecessary repetition of entire workflows, thereby improving overall computational stability.

At step 306, omni-agent 103 may invoke self-healing routines when a stalled, nonresponsive, or corrupted agent is detected. Self-healing may include warm-restarting an agent container, resetting GPU kernels, refreshing device memory buffers, reinitializing communication channels, or migrating execution to redundant hardware nodes. Omni-agent 103 may use watchdog timers to monitor the liveness of each agent. A missing heartbeat signal may trigger automatic teardown and reinitialization of the affected component. In some embodiments, the system may employ a checkpointing mechanism that stores periodic snapshots of the shared-state memory object, including version identifiers, tensor metadata, and execution-state descriptors. These checkpoints provide a reliable restoration point that can be used to resume processing after a system failure without restarting the entire workflow. Such self-healing behaviors constitute concrete technical remedies that improve system reliability in distributed and heterogeneous computing environments.

If the routing decision permits normal processing to continue, omni-agent 103 proceeds to step 307, where it invokes one or more downstream agents identified in the workflow graph. When doing so, omni-agent 103 may perform device-placement optimization to determine the most efficient compute device for each agent. The selection may consider the agent's memory footprint, expected kernel execution time, model size, parallelism level, and estimated workloads. On edge devices, omni-agent 103 may use NUMA-aware scheduling to reduce cache-line contention and ensure that memory access paths remain local to the executing CPU or GPU. Invocation of agents may include transmitting updated subsets of the shared-state memory object, initializing agent-specific configuration parameters, and allocating or prewarming necessary compute buffers.

At step 308, omni-agent 103 aggregates outputs from multiple downstream agents. Aggregation may require device-to-device communication using technologies such as NVLink or PCIe peer access, enabling tensors residing on separate GPUs to be fused without host mediation. Aggregation may employ fused kernels that combine concatenation, weighting, normalization, and alignment operations into a single GPU-executed procedure. Such fused kernels reduce memory overhead, minimize host-device data transfers, and eliminate redundant intermediate tensors. Aggregation may also incorporate conflict-resolution logic that compares confidence scores, uncertainty values, and modality-specific metrics to construct a unified clinical representation from multiple agent outputs.

The workflow concludes at step 309, where omni-agent 103 finalizes processing for the current iteration. Completion may include updating patient-level inference records within a transactional write-ahead log that ensures atomic persistence across hardware faults or restarts. The system may record the specific agent sequence executed, the device placement decisions, the confidence evaluations, and the routing decisions. This audit log enables regulatory, clinical, and operational traceability. In some embodiments, the completion step may also trigger asynchronous processes, including federated-learning updates, cloud-synchronization tasks, governance audit routines, model-regression tests using simulated clinical scenarios, or long-term reliability monitoring. The completion step therefore ensures that each inference workflow terminates in a reproducible, auditable, and clinically interpretable state.

Figure 4:
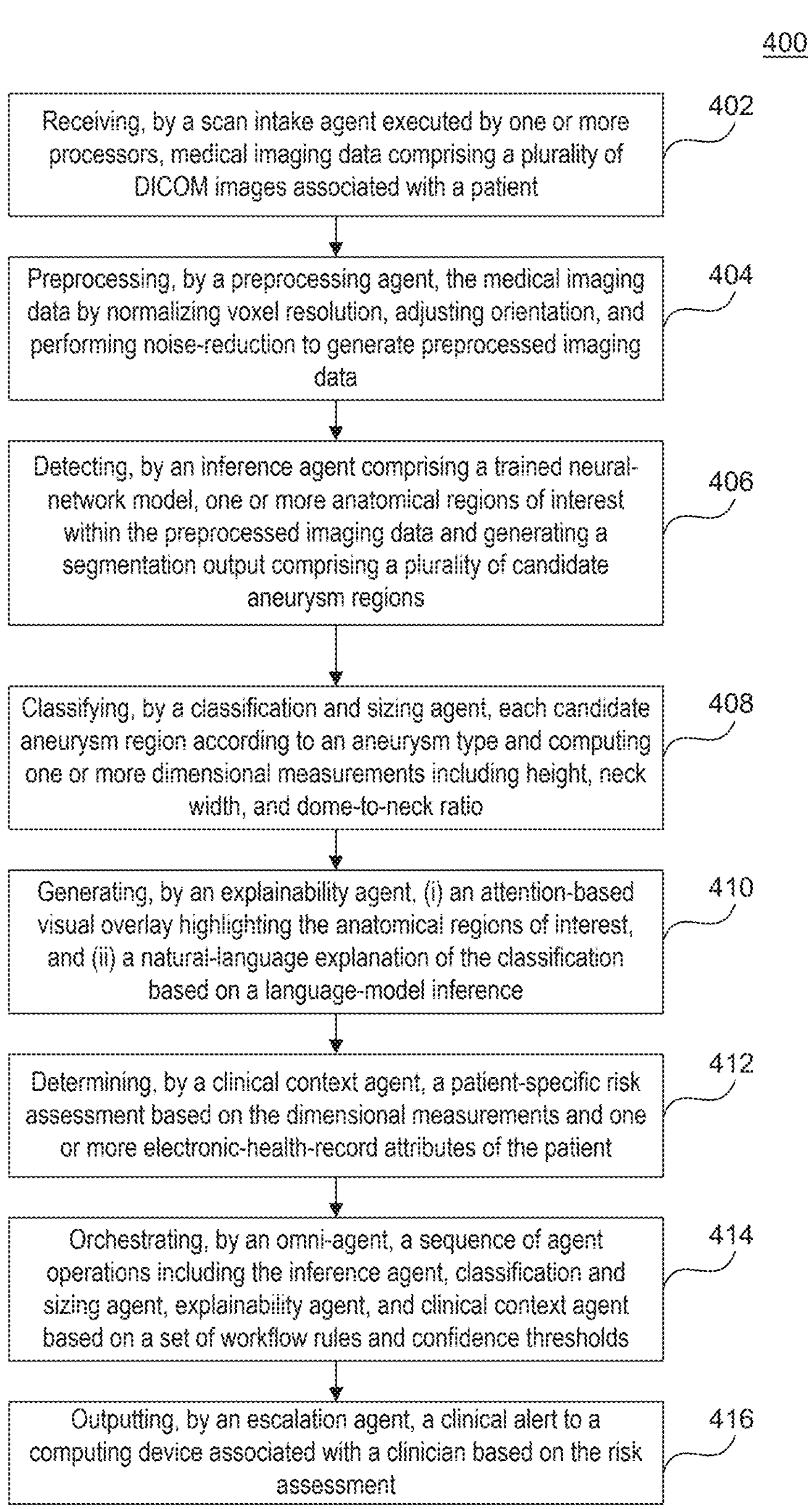
FIG. 4 illustrates an example flow diagram for performing multi-stage medical image preprocessing and neural-network inference, according to some aspects.

FIG. 4 illustrates a flowchart 400 of a computer-implemented method for multi-agent medical imaging analysis, according to some embodiments. The flowchart 400 may demonstrate the sequential execution of specialized agents in an orchestrated workflow designed to process medical imaging data and generate comprehensive clinical decision-support outputs. This method may represent a significant advancement over conventional monolithic medical AI systems by implementing a modular, agent-based architecture that can enable dynamic routing, parallel processing, and adaptive workflow management based on intermediate confidence scores and clinical priorities.

Method 400 can be performed by processing logic that can comprise hardware (e.g., circuitry, dedicated logic, programmable logic, microcode, etc.), software (e.g., instructions executing on a processing device), or a combination thereof. It is to be appreciated that not all steps may be needed to perform the disclosure provided herein. Further, some of the steps may be performed simultaneously, or in a different order than shown in FIG. 4, as will be understood by a person of ordinary skill in the art.

Method 400 shall be described with reference to FIG. 1. However, method 400 is not limited to that example embodiment.

At step 402, the method may begin with receiving, by scan intake agent 104 executed by one or more processors 102, medical imaging data comprising a plurality of DICOM images associated with a patient. Scan intake agent 104 may serve as the initial validation and quality control gateway for the entire multi-agent workflow within multi-agent medical imaging system 100. In some embodiments, scan intake agent 104 may validate imaging format compatibility, which can include DICOM, NIfTI, or proprietary scanner formats from manufacturers such as GE, Siemens, Philips, or Canon. Scan intake agent 104 may perform comprehensive metadata extraction, which can include scanner-model identifiers, acquisition protocols, slice thickness, field of view, contrast agent usage, and patient positioning parameters. For example, in a brain aneurysm detection scenario, scan intake agent 104 may validate that CT angiography images contain appropriate contrast enhancement phases and sufficient spatial resolution for vascular analysis.

Scan intake agent 104 may also perform study completeness assessment by verifying that all required image series are present and properly ordered. In some embodiments, this may include checking for pre-contrast and post-contrast phases in CT angiography studies, or ensuring that multiplanar reconstructions are available for comprehensive anatomical evaluation. Scan intake agent 104 may also validate anonymization status to ensure HIPAA compliance, removing or masking patient identifiers while preserving clinically relevant metadata such as age, gender, and relevant medical history indicators that may influence diagnostic algorithms.

In alternative embodiments, scan intake agent 104 may be configured to handle multi-modal imaging studies simultaneously. For instance, in stroke evaluation protocols, scan intake agent 104 may process both CT perfusion and CT angiography datasets, validating temporal synchronization between acquisitions and ensuring that perfusion maps and vascular imaging are properly aligned for subsequent analysis. Scan intake agent 104 may also implement quality scoring algorithms that can assess image noise levels, motion artifacts, and contrast enhancement adequacy, providing quality metrics that may influence downstream agent selection and processing parameters.

At step 404, preprocessing may be performed by preprocessing agent 106 on the medical imaging data by normalizing voxel resolution, adjusting orientation, and performing noise-reduction to generate preprocessed imaging data. Preprocessing agent 106 may implement sophisticated image enhancement and standardization algorithms essential for reliable machine learning inference. In some embodiments, voxel normalization may involve resampling images to standardized grid dimensions, such as 1 $mm^3$ isotropic voxels for brain imaging or 0.5 $mm^3$ for high-resolution vascular analysis. This standardization may ensure consistent input dimensions for neural network models regardless of the original scanner acquisition parameters.

Orientation alignment may represent a critical preprocessing step that transforms images to standard anatomical coordinate systems. For brain imaging, this may typically involve alignment to the AC-PC (anterior commissure-posterior commissure) line or Montreal Neurological Institute (MNI) space. Preprocessing agent 106 may employ rigid body transformations, affine registration, or non-linear deformation algorithms to achieve optimal anatomical alignment. In some embodiments, preprocessing agent 106 may utilize deep learning-based registration networks that can rapidly align images while preserving anatomical detail and pathological features.

Noise reduction algorithms implemented by preprocessing agent 106 may include traditional filtering techniques such as Gaussian smoothing, anisotropic diffusion, or advanced deep learning-based denoising networks. For example, in low-dose CT imaging scenarios common in emergency stroke evaluation, preprocessing agent 106 may apply specialized denoising algorithms that preserve vascular detail while reducing quantum noise artifacts. Preprocessing agent 106 may also perform skull stripping for brain imaging studies, utilizing algorithms such as FSL's Brain Extraction Tool (BET) or deep learning-based skull stripping networks that can accurately separate brain tissue from skull and scalp.

In alternative embodiments, preprocessing agent 106 may implement modality-specific enhancement algorithms. For CT angiography, this could include vessel enhancement filtering using Hessian-based multiscale analysis or machine learning-based vessel segmentation preprocessing. For MRI studies, preprocessing agent 106 may perform bias field correction, intensity normalization across different pulse sequences, and motion correction for multi-sequence acquisitions. Preprocessing agent 106 may also generate derived image products, such as maximum intensity projections (MIP) or curved planar reconstructions, that may facilitate subsequent analysis by specialized inference agents.

At step 406, detecting may be performed by inference agent 108 comprising a trained neural-network model to identify one or more anatomical regions of interest within the preprocessed imaging data and generate a segmentation output comprising a plurality of candidate abnormality regions. Inference agent 108 may represent the core artificial intelligence component of multi-agent medical imaging system 100, implementing state-of-the-art deep learning architectures for medical image analysis. In some embodiments, inference agent 108 may utilize U-Net architectures, three-dimensional convolutional neural networks, transformer-based models, or hybrid architectures that combine multiple network types for optimal performance.

For brain aneurysm detection, inference agent 108 may implement a cascaded detection and segmentation approach. The initial detection network may identify potential aneurysm locations using object detection frameworks such as YOLO (You Only Look Once) or R-CNN (Region-based Convolutional Neural Network) adapted for medical imaging. Subsequently, a specialized segmentation network, such as a 3D U-Net or attention-based segmentation model, may generate precise pixel-level or voxel-level masks delineating aneurysm boundaries. Inference agent 108 may output confidence scores for each detected region, enabling downstream agents to prioritize high-confidence findings and flag uncertain cases for additional analysis.

In some embodiments, inference agent 108 may implement ensemble methods that combine predictions from multiple neural network architectures to improve robustness and accuracy. For example, inference agent 108 may utilize both convolutional neural networks optimized for spatial feature extraction and transformer networks that excel at capturing long-range dependencies in medical images. The ensemble approach may also incorporate uncertainty quantification techniques, such as Monte Carlo dropout or Bayesian neural networks, that can provide confidence intervals for predictions and enable more sophisticated downstream decision-making.

Inference agent 108 may also generate multiple output formats to support diverse clinical workflows. In addition to segmentation masks, inference agent 108 may produce bounding volumes that encompass detected abnormalities, surface meshes for three-dimensional visualization, and probability maps that indicate the likelihood of pathology at each image location. For vascular imaging applications, inference agent 108 may generate centerline extractions, vessel diameter measurements, and tortuosity indices that can provide quantitative assessments of vascular geometry and pathology.

At step 408, classifying may be performed by classification and sizing agent 110 on each candidate abnormality region according to a lesion type and by computing one or more dimensional measurements that may include height, width, depth, volume, curvature metrics, shape descriptors, or surface-to-base ratio. Classification and sizing agent 110 may extract these morphological properties directly from the three-dimensional tensor representations produced by inference agent 102 or segmentation agent 108, and may utilize multi-axis interpolation, mesh reconstruction, or voxel-based fitting techniques to ensure accurate measurement even when imaging artifacts or partial-volume effects are present. The agent may produce detailed morphological profiles that are essential for clinical decision-making, longitudinal tracking, and risk stratification.

For aneurysm analysis, classification and sizing agent 110 may classify detected lesions according to established morphological categories such as saccular, fusiform, or dissecting aneurysms, each of which may carry distinct implications for rupture risk, intervention strategy, and follow-up schedules. In some embodiments, the agent may also detect features such as wall irregularity, dome-to-neck ratio, daughter sacs, thrombosed regions, or surface roughness that further inform clinical planning.

Although aneurysm characterization represents one exemplary use case, other types of detections may likewise be performed. For example, classification and sizing agent 110 may identify and characterize pulmonary nodules, hepatic lesions, renal masses, vertebral fractures, cardiac chamber abnormalities, or soft-tissue tumors. In these applications, the agent may employ domain-specific taxonomies, such as Lung-RADS categories for pulmonary nodules or BI-RADS categories for breast lesions, and may compute specialized morphometric features including spiculation indices, margin sharpness, attenuation patterns, cavitation probability, or vascular encasement. The agent may also integrate multimodal information such as contrast-enhancement curves, diffusion metrics, or metabolic-activity measurements when available from corresponding MRI, CT, PET, or ultrasound acquisitions. Through these capabilities, classification and sizing agent 110 supports a broad range of clinical detection tasks and provides a consistent framework for extracting clinically relevant morphometric features across diverse disease domains and imaging modalities.

Dimensional measurements computed by classification and sizing agent 110 may include traditional metrics such as maximum diameter, neck width, and dome-to-neck ratio, which can be critical for determining treatment eligibility and approach selection. Classification and sizing agent 110 may also compute advanced shape descriptors including sphericity indices, compactness measures, surface irregularity metrics, and aspect ratios that can provide more comprehensive morphological characterization. In some embodiments, classification and sizing agent 110 may generate three-dimensional reconstructions that enable precise volumetric measurements and surface area calculations, supporting advanced biomechanical analysis and rupture risk assessment.

Classification and sizing agent 110 may implement machine learning-based feature extraction algorithms that identify subtle morphological patterns associated with clinical outcomes. For example, classification and sizing agent 110 may utilize radiomic analysis techniques that extract hundreds of quantitative features from medical images, including first-order statistics, texture features, and wavelet-based descriptors. These features may be combined using machine learning classifiers to predict clinical outcomes such as aneurysm growth rates, rupture risk, or treatment response.

In alternative embodiments, classification and sizing agent 110 may be configured for multi-pathology analysis. For stroke imaging, classification and sizing agent 110 may classify detected lesions as acute infarcts, chronic infarcts, hemorrhages, or other pathological findings, computing relevant measurements such as infarct volume, hemorrhage volume, and midline shift measurements. Classification and sizing agent 110 may also perform temporal analysis for longitudinal studies, tracking changes in lesion size, morphology, and characteristics over time to assess disease progression or treatment response.

At step 410, generating may be performed by explainability agent 112 to produce (i) an attention-based visual overlay highlighting the anatomical regions of interest, and (ii) a natural-language explanation of the classification based on a language-model inference. Explainability agent 112 may address the critical need for interpretable AI in medical applications by providing both visual and textual explanations of algorithmic decisions. The attention-based visual overlays may utilize techniques such as Grad-CAM (Gradient-weighted Class Activation Mapping), saliency mapping, or attention visualization to highlight image regions that most strongly influenced the AI's diagnostic conclusions.

For brain aneurysm detection, explainability agent 112 may generate heat maps or saliency overlays that highlight vascular regions exhibiting morphological features characteristic of aneurysms, including focal dilatations, irregular wall contours, asymmetric vessel expansions, or abnormal branching geometries. These visual explanations may be derived from intermediate activations, gradient-based attribution methods, class-activation mappings, or attention-weight distributions extracted directly from the neural networks used by inference agent 102. The visual overlays may be rendered at multiple scales, beginning with coarse representations that identify the general vascular territory containing the suspected abnormality and progressing to fine-grained close-up views that delineate neck regions, dome boundaries, wall irregularities, or associated vascular branches. In some embodiments, explainability agent 112 may generate three-dimensional attribution volumes that reflect voxel-wise contribution scores across the entire CT or MR angiographic dataset, allowing clinicians to manipulate, rotate, slice, and zoom through the attribution field in an interactive interface to better understand model reasoning.

In certain implementations, explainability agent 112 may incorporate temporal or cross-modality alignment in cases where multiple imaging studies are available, such as CT angiography paired with MR angiography or perfusion imaging. In such embodiments, the agent may generate synchronized overlays that show how the model weighted corresponding anatomical regions across modalities, thereby strengthening clinical interpretability. The agent may also quantify explanation fidelity by computing metrics such as consistency between heat-map intensities and segmentation boundaries, or by comparing attribution distributions across repeated inference passes to detect instability or model brittleness.

Although brain aneurysm detection represents an exemplary use case, explainability agent 112 may produce analogous visual or numerical explanations for a wide variety of clinical detection tasks. For example, the agent may generate saliency maps for pulmonary nodule classification that highlight spiculation patterns or attenuation gradients, provide attention overlays for breast-lesion analysis that emphasize mass margins or calcification clusters, or generate metabolic-signal attribution maps for PET imaging that reflect SUV-weighted feature contributions. In musculoskeletal applications, explainability agent 112 may highlight fracture lines, cortical irregularities, or ligamentous disruptions. In abdominal imaging, the agent may emphasize rim enhancement, capsular retraction, lesion wash-in and wash-out patterns, or perilesional edema. The agent may further support non-imaging modalities by generating text-attention visualizations for EHR-derived features or gene-importance profiles for genomic predictors.

Through these capabilities, explainability agent 112 provides a unified, technically rigorous framework for generating interpretable, clinically meaningful explanations for diverse types of detections, thereby improving model transparency, facilitating clinician trust, and supporting regulatory auditability across multiple imaging modalities and disease domains The natural-language explanation component of explainability agent 112 may utilize large language models (LLMs) trained on medical literature and clinical reports to generate human-readable descriptions of diagnostic findings. For example, explainability agent 112 may generate explanations such as "A 7 mm saccular aneurysm is identified at the anterior communicating artery with a dome-to-neck ratio of 2.1, suggesting increased rupture risk based on morphological criteria." The language model component may be fine-tuned on domain-specific medical terminology and clinical reasoning patterns to ensure accuracy and clinical relevance.

In some embodiments, explainability agent 112 may implement consistency validation mechanisms that verify agreement between visual attention maps and natural-language explanations. This may involve semantic parsing of generated text to extract anatomical locations and pathological descriptors, followed by comparison with attention map localizations to ensure coherent explanations. Explainability agent 112 may also adapt explanation complexity based on the intended audience, providing detailed technical descriptions for radiologists while generating simplified summaries for referring clinicians or patient communication.

At step 412, determining may be performed by clinical context agent 114 to compute a patient-specific risk assessment based on the dimensional measurements and one or more electronic-health-record attributes of the patient. Clinical context agent 114 may integrate imaging-derived findings with broader clinical information to provide comprehensive risk stratification and treatment recommendations. Clinical context agent 114 may access electronic health record (EHR) data including patient demographics, medical history, current medications, laboratory results, and prior imaging studies to contextualize current findings within the patient's overall clinical picture.

For aneurysm risk assessment, clinical context agent 114 may implement established clinical scoring systems such as PHASES (Population, Hypertension, Age, Size, Earlier subarachnoid hemorrhage, Site) or UJATS (Unruptured Intracranial Aneurysm Treatment Score), each of which integrates multiple imaging-derived variables with patient-specific clinical risk factors to estimate rupture probability and guide treatment recommendations. In some embodiments, clinical context agent 114 may automatically extract the constituent PHASES and UJATS components from the shared-state memory object that aggregates imaging measurements, demographic information, comorbidity data, and prior clinical history. The agent may compute weighted subscores for each relevant factor, perform consistency checks to detect missing or implausible values, and produce a final composite risk score along with explanatory breakdowns that reflect the relative contribution of each feature. The agent may further incorporate domain-specific normalization procedures, such as adjusting risk estimates based on scanner type, contrast protocol, or volumetric sizing method, to ensure consistent scoring across heterogeneous imaging datasets. Clinical context agent 114 may perform longitudinal analysis by comparing current findings with prior imaging studies to assess aneurysm growth rates, morphological changes, or new lesion development. This temporal analysis may provide crucial information for treatment decision-making, as aneurysm growth can be a strong predictor of rupture risk. Clinical context agent 114 may also integrate genetic risk factors, family history, and lifestyle factors that may influence aneurysm development and progression.

In alternative embodiments, clinical context agent 114 may be configured for broader clinical decision support beyond aneurysm analysis. For stroke evaluation, clinical context agent 114 may integrate imaging findings with clinical stroke scales (such as NIHSS), onset time, and contraindications to specific treatments to provide treatment recommendations and outcome predictions. Clinical context agent 114 may also consider institutional protocols, resource availability, and patient preferences in generating personalized treatment recommendations.

In certain implementations, clinical context agent 114 may augment or replace traditional scoring systems with machine-learning-based risk models trained on large, multi-institutional datasets that include imaging features, quantitative shape descriptors, hemodynamic surrogates, laboratory findings, longitudinal EHR data, and relevant demographic attributes. These models may include gradient-boosted decision trees, random forests, logistic regression ensembles, deep neural networks, or hybrid architectures capable of fusing multimodal features into unified representations. The agent may perform feature scaling, imputation, one-hot encoding, longitudinal feature aggregation, time-series processing, or graph-based patient-trajectory analysis as part of the risk modeling pipeline. In some embodiments, the agent may generate confidence intervals or uncertainty bounds associated with each predicted risk level using bootstrap resampling, Monte Carlo dropout sampling, or deep ensemble aggregation.

Although aneurysm risk or stroke assessment represents two exemplary applications, clinical context agent 114 may be configured to perform analogous clinical scoring and risk stratification tasks for a wide range of disease domains. For pulmonary nodule assessment, the agent may implement validated scoring systems such as BROCK or the Mayo model, or may utilize machine-learning-based malignancy predictors derived from nodule morphology, radiomic features, growth trajectories, and smoking history. For cardiac imaging, the agent may compute clinical metrics such as ejection fraction, chamber volumes, coronary calcium scores, or HEART/TIMI risk scores by integrating imaging findings with clinical history and biomarker data. For oncology workflows, the agent may apply RECIST criteria, tumor staging guidelines, or machine-learning-based survival predictors that consider tumor burden, metabolic activity, genomic markers, and treatment history. In musculoskeletal imaging, the agent may assess fracture risk, grade ligamentous injuries, or evaluate degenerative changes by combining imaging measurements with patient age, activity level, bone density values, and prior injury history. Through these capabilities, clinical context agent 114 provides a flexible and technically robust framework for merging imaging-derived insights with structured clinical data, enabling consistent, interpretable, and high-fidelity risk assessments across diverse medical conditions and imaging modalities At step 414, orchestrating may be performed by omni-agent 116 to coordinate a sequence of agent operations including inference agent 108, classification and sizing agent 110, explainability agent 112, and clinical context agent 114 based on a set of workflow rules and confidence thresholds. Omni-agent 116 may serve as the central coordination hub that manages the entire multi-agent workflow within multi-agent medical imaging system 100, making dynamic decisions about agent execution order, parallel processing opportunities, and quality control measures. Omni-agent 116 may implement sophisticated workflow management algorithms that optimize processing efficiency while ensuring clinical accuracy and reliability.

Omni-agent 116 may utilize confidence thresholds to determine when additional processing steps are required. For example, if inference agent 108 produces low-confidence segmentations, omni-agent 116 may trigger re-processing with alternative neural network architectures, invoke ensemble methods, or route cases for manual review. Omni-agent 116 may also implement adaptive workflow routing based on imaging characteristics, clinical urgency, or institutional protocols. In some embodiments, omni-agent 116 may maintain shared-state memory object 118 that stores intermediate results, metadata, provenance information, and workflow status indicators. This shared state may enable sophisticated coordination between agents and support advanced features such as workflow rollback, alternative processing pathways, and quality assurance checks. Omni-agent 116 may also implement parallel execution strategies that simultaneously invoke multiple specialized agents when computational resources permit, significantly reducing overall processing time.

Omni-agent 116 may incorporate machine learning-based workflow optimization that learns from historical processing patterns and outcomes to improve future workflow decisions. For example, omni-agent 116 may learn that certain imaging characteristics are associated with higher inference accuracy, enabling preemptive quality control measures or alternative processing strategies for challenging cases.

At step 416, outputting may be performed by escalation agent 120 to generate a clinical alert to a computing device associated with a clinician based on the risk assessment. Escalation agent 120 may implement intelligent triage and notification systems that ensure appropriate clinical response to urgent findings. Escalation agent 120 may generate tiered alert levels, such as urgent, semi-urgent, or routine, based on risk assessment scores, clinical context, and institutional protocols.

For high-risk aneurysm findings, escalation agent 120 may generate immediate notifications to neurosurgeons, interventional neuroradiologists, critical-care specialists, and emergency department physicians using multiple communication channels including hospital paging systems, secure clinical-messaging platforms, electronic health-record alert frameworks, and mobile push-notification services. In some embodiments, escalation agent 120 may interface directly with institutional communication middleware such as message buses, on-call scheduling systems, or clinician-directory services to dynamically determine the appropriate recipient list based on specialty, shift schedule, credentialing, or geographic coverage. The agent may embed structured metadata within each alert, including lesion location, morphological characteristics, rupture-risk estimates, uncertainty values, and links to explainability visualizations generated by explainability agent 112, thereby ensuring that receiving clinicians obtain clinically actionable context without needing to manually retrieve upstream imaging results.

Escalation agent 120 may additionally implement time-aware escalation protocols that automatically notify secondary or tertiary clinicians if primary contacts do not acknowledge or respond to an alert within defined time thresholds. These time thresholds may vary based on clinical urgency, predicted rupture risk, patient comorbidities, or institutional service-level policies, and may be adjusted dynamically according to real-time monitoring of clinician availability. In certain implementations, the agent may track acknowledgment events using cryptographically signed confirmation tokens, thereby ensuring verifiable auditability for regulatory and clinical-governance purposes. If escalation involves multiple tiers of clinicians, the agent may coordinate alert delivery using distributed queuing mechanisms and acknowledgment-tracking state machines that prevent redundant notifications, racing conditions, or acknowledgment conflicts.

Although aneurysm detection represents one exemplary scenario, escalation agent 120 may implement analogous escalation workflows for other high-risk clinical findings. For example, the agent may escalate pulmonary embolism detections to pulmonary and vascular specialists, intracranial hemorrhages to stroke teams, malignant lesion findings to oncology or radiology rapid-response teams, and acute cardiac abnormalities to cardiology services. In each domain, escalation agent 120 may fuse imaging-derived risk indicators with clinical context supplied by clinical context agent 114 to determine the appropriate escalation tier and timing. Through these capabilities, escalation agent 120 provides a technically robust, auditable, and latency-sensitive communication mechanism that integrates tightly with the multi-agent architecture of system 100 and supports rapid clinical intervention across diverse diagnostic workflows.

Escalation agent 120 may generate structured clinical decision-support messages that include segmentation visualizations, quantitative measurements, risk scores, and treatment recommendations. These messages may be formatted for integration with existing clinical workflows and electronic health record systems, supporting seamless incorporation into clinical decision-making processes. Escalation agent 120 may also generate patient-friendly summaries that can be used for patient education and shared decision-making discussions.

In alternative embodiments, escalation agent 120 may implement advanced communication features such as real-time collaboration tools that enable multi-disciplinary team discussions around complex cases. Escalation agent 120 may also support telemedicine workflows by generating comprehensive case packages that can be transmitted to remote specialists for consultation and treatment planning.

This multi-agent architecture may provide significant advantages over conventional medical AI systems by enabling modular, scalable, and adaptive processing workflows. Multi-agent medical imaging system 100 may accommodate new imaging modalities, updated algorithms, and evolving clinical protocols through the addition or modification of individual agents without requiring complete system redesign. The orchestrated approach may also enable sophisticated quality control, uncertainty quantification, and clinical decision support that significantly enhances the reliability and clinical utility of AI-assisted medical imaging analysis.

Figure 5:
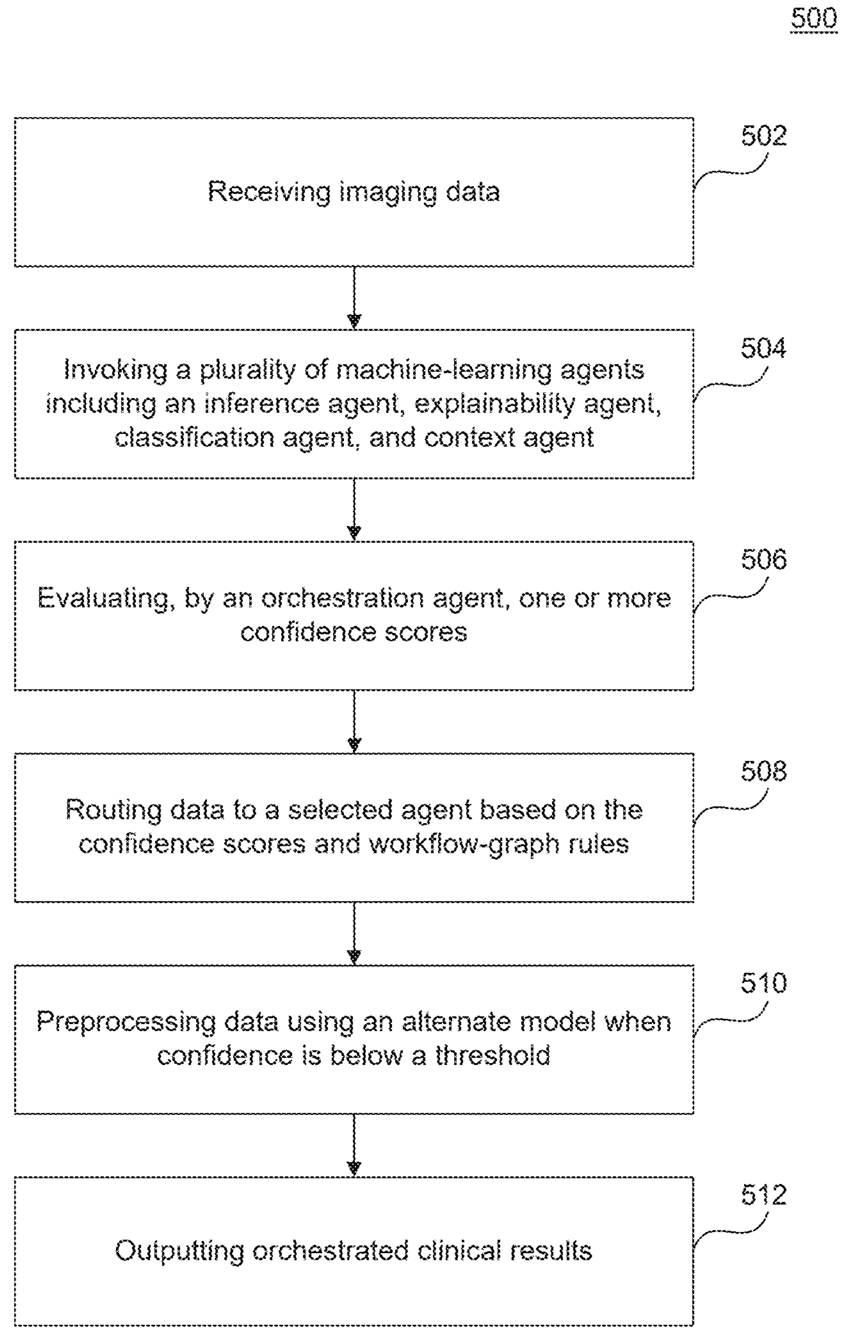
FIG. 5 illustrates another example flow diagram for generating a structured clinical decision-support output, according to some aspects.
Figure 6:
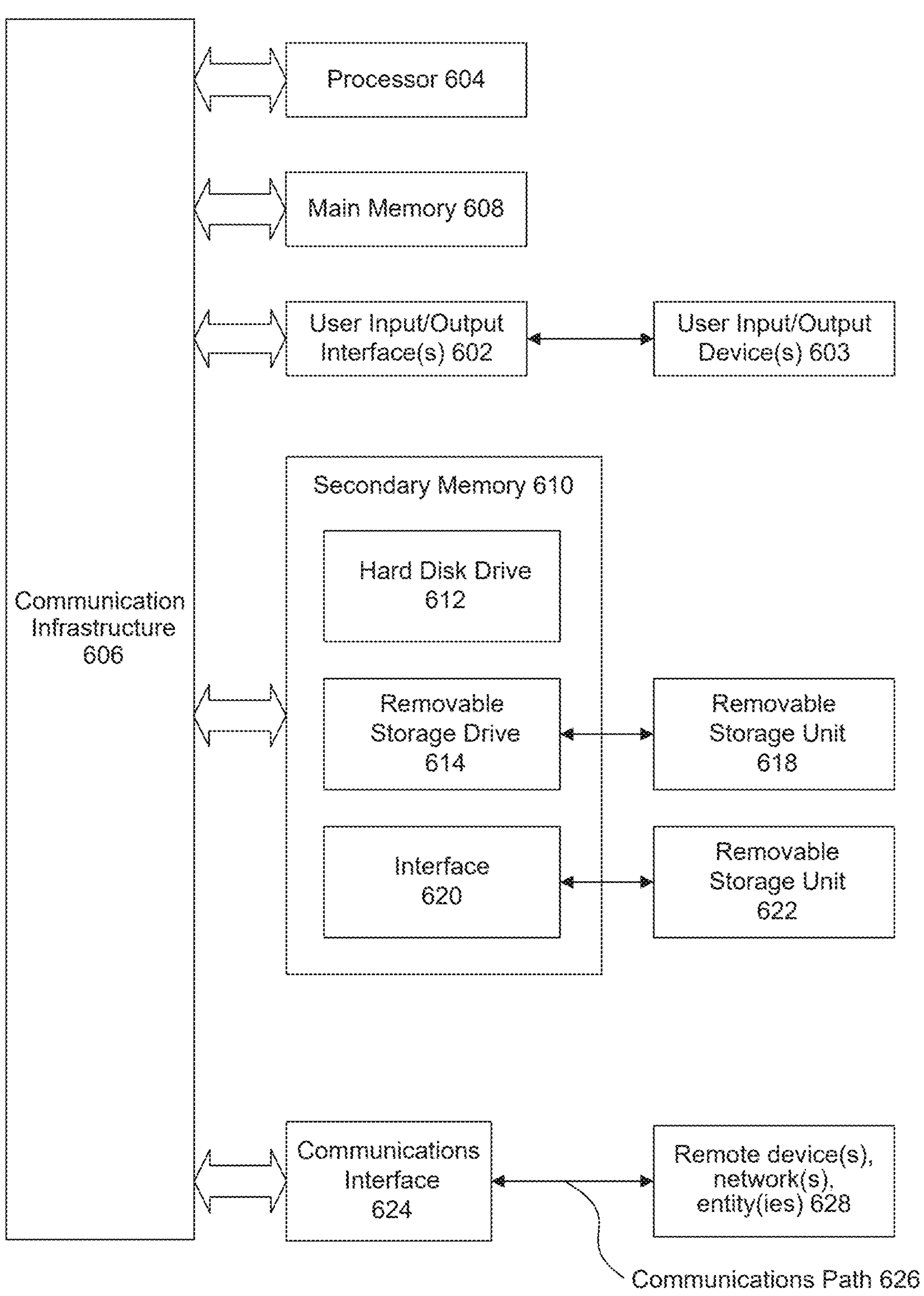
FIG. 6 illustrates an example computer system useful for implementing various aspects, according to some aspects.

FIG. 5 illustrates an exemplary method 500 for orchestrating a multi-agent medical-imaging analysis pipeline using an adaptive routing architecture driven by confidence evaluation, workflow-graph logic, memory-aware scheduling, and hardware-assisted computational optimization. The method begins at step 502, where imaging data is received from one or more acquisition systems. The imaging data may include computed-tomography angiography volumes, magnetic-resonance angiography datasets, ultrasound Doppler sequences, or other modality-specific imaging representations. In certain embodiments, the imaging data may be streamed directly from scanner consoles or PACS servers into a shared-state memory buffer that is implemented using zero-copy serialization formats or direct-access device memory, allowing the data to be written once and accessed by multiple agents without redundant copying. The receiving subsystem may normalize coordinate spaces, decode DICOM headers, validate voxel dimensions, extract protocol metadata, and detect malformed series or incomplete image stacks using tensor-shape consistency checks, header-level anomaly detection, and voxel-spacing validation. These operations reduce the likelihood of downstream inference failures and provide a technical improvement in computational reliability for high-throughput imaging workflows.

At step 504, the system invokes a plurality of machine-learning agents, which may include an inference agent, an explainability agent, a classification agent, and a clinical context agent. Each agent may operate on specific regions of the shared-state memory object, which may include large multi-dimensional tensors stored in pinned host memory or device-resident GPU memory. Prior to invocation, omni-agent 103 may perform device-placement selection to assign each agent to a particular GPU, TPU, or CPU vector unit based on predicted memory footprint, expected kernel-execution time, and overall resource availability. The inference agent may apply segmentation networks, detection models, or volumetric transformer architectures to identify candidate abnormality regions. The explainability agent may compute saliency volumes, feature-attribution maps, or intermediate neural activations directly on device memory to avoid unnecessary host-device transfers. The classification agent may compute volumetric and morphological measurements, and the clinical context agent may retrieve and integrate EHR-derived attributes, laboratory measurements, temporal histories, and demographic modifiers. This multi-agent invocation constitutes the initial analytical phase of the orchestrated workflow and leverages accelerated hardware resources to improve computational throughput.

At step 506, the system evaluates one or more confidence scores produced by the machine-learning agents using an orchestration agent such as omni-agent 103. Confidence evaluation may consider predictive entropy, mutual-information estimates, calibration-curve alignment, reconstruction consistency, or other uncertainty metrics derived from inference outputs. The orchestration agent may further incorporate system telemetry signals collected from the execution environment, such as GPU utilization, kernel latency, memory fragmentation, queue depth, CPU load, and I/O bandwidth. These telemetry metrics may be sampled at sub-millisecond intervals and fed into the routing logic to detect potential performance bottlenecks or early signs of computational instability. Confidence evaluation may also identify malformed tensors, missing slices, activation outliers, or CUDA kernel error codes. When such anomalies are detected, the orchestration agent may preemptively redirect execution paths to alternative workflows, providing a technical mechanism for reducing system failures in large-model medical-processing environments.

At step 508, the orchestration agent routes the data to one or more selected downstream agents according to both the aggregated confidence scores and the logic encoded within the workflow graph. The workflow graph may encode modality-specific dependencies, execution constraints, and conditional rules that define permissible transitions among agents. Routing decisions may consider lesion type, clinical urgency, expected resource consumption, and agreement between outputs of different agents, such as consistency between segmentation boundaries and attribution maps. Routing decisions may be recalculated dynamically as new results become available, allowing the workflow to adjust in real time to changing computational conditions or newly discovered discrepancies. This dynamic routing behavior improves system robustness compared to conventional fixed pipelines and provides a concrete improvement in resource allocation, execution stability, and inference reliability.

At step 510, when the evaluated confidence falls below a predefined threshold, the system may preprocess or reprocess the data using an alternate model or corrective sub-pipeline. The alternate model may include robustness-optimized convolutional networks, denoising autoencoders, artifact-removal models, or pruned and quantized neural networks designed for execution on limited compute budgets. During this stage, the system may regenerate regions of interest, apply spatial interpolation to missing slices, correct slice-thickness inconsistencies, mitigate motion artifacts, or adjust for contrast-timing deviations using acquisition metadata extracted from DICOM headers. When the imaging data exceeds available GPU memory, preprocessing may occur in spatial partitions using streaming kernels with overlap margins to preserve convolutional continuity. These corrective processes allow the system to recover from degraded or corrupted imaging inputs without discarding prior work or requiring a full pipeline restart.

In addition to model-based correction, memory usage and storage allocation may be actively managed during step 510. The system may monitor memory usage across GPU and host memory pools using fine-grained counters and perform memory compaction or deallocation of unused buffers prior to invoking fallback networks. Alternate models may be executed using lower-precision tensor formats such as FP16 or INT8 when memory pressure is detected. The shared-state memory object may maintain a tensor-access manifest that records which agents have consumed or produced each intermediate result, allowing omni-agent 103 to avoid redundant recomputation and prevent unnecessary data duplication. These memory-aware scheduling and storage-management capabilities represent specific improvements to computer performance and reduce latency in resource-constrained environments.

At step 512, the system outputs orchestrated clinical results generated by the multi-agent pipeline. The output may include lesion-detection coordinates, segmentation masks, dimensional and morphological measurements, clinical-risk estimates, uncertainty metrics, and explainability overlays. These results may be written into a transactional write-ahead log stored in SSD-backed persistent volumes, ensuring atomicity and recoverability in the event of system interruption. The output may be transmitted to radiology workstations, clinical dashboards, electronic health records, or escalation agent 120 for urgent clinical notification. In distributed deployments, outputs may be propagated to federated nodes using secure channels that support write-consistency and version tracking. The completion of this step ensures that the entire multi-agent workflow yields a reproducible, auditable, and clinically interpretable result, thereby constituting a concrete improvement in the integrity and reliability of computer-driven medical-imaging analysis.

FIG. 7 illustrates a computer system 700 that may be used to implement the multi-agent medical imaging analysis system described herein, according to some embodiments. Computer system 700 may represent a comprehensive computing infrastructure capable of executing the orchestrated agent-based workflow for medical data processing, clinical decision support, and automated diagnostic analysis. The system may provide the necessary hardware and software foundation to support the complex multi-agent architecture, including scan intake, preprocessing, inference, explainability, bias detection, clinical context analysis, risk scoring, and escalation agents described throughout this disclosure.

Computer system 700 may include processor 704, main memory 708, user input/output interface(s) 702, user input/output device(s) 703, secondary memory 710, communications interface 624, and communication infrastructure 706. Communication infrastructure 706 may be a bus, crossbar switch, network, or other mechanism for enabling the various components of computer system 700 to communicate with each other. Communication infrastructure 706 may support high-bandwidth data transfer required for processing large medical imaging datasets, which may include CT scans, MRI images, ultrasound data, digital pathology slides, and multimodal clinical data.

Processor 704 may be one or more central processing units (CPUs), graphics processing units (GPUs), tensor processing units (TPUs), or other specialized processors configured to execute the multi-agent medical imaging analysis system. In some embodiments, processor 704 may comprise multiple CPU cores optimized for parallel processing of agent workflows. For example, processor 704 may include Intel Xeon processors, AMD EPYC processors, or ARM-based processors capable of handling computationally intensive machine learning inference operations. In embodiments requiring accelerated neural network processing, processor 704 may include NVIDIA Tesla V100, A100, or H100 GPUs specifically designed for deep learning workloads. The processor architecture may support CUDA, OpenCL, or other parallel computing frameworks necessary for executing convolutional neural networks, U-Net architectures, transformer models, and hybrid AI models used by the inference agent.

Processor 704 may execute instructions stored in main memory 708 to implement the orchestration agent (omni-agent), which may serve as the central coordinator for the multi-agent workflow. The orchestration agent may dynamically allocate processor resources among specialized agents based on confidence scores, workflow conditions, and system load. For instance, when the inference agent generates low-confidence segmentation results, processor 704 may reallocate computational resources to execute alternative neural networks or trigger parallel execution of multiple specialized agents. In embodiments supporting real-time medical imaging analysis, processor 704 may implement priority-based scheduling to ensure that critical findings, such as aneurysm detection or stroke identification, receive immediate processing attention.

Main memory 708 may be random access memory (RAM), dynamic RAM (DRAM), static RAM (SRAM), or other volatile memory configured to store program instructions and data during system operation. Main memory 708 may have sufficient capacity to hold large medical imaging datasets, neural network models, and intermediate processing results generated by specialized agents. For example, main memory 708 may include 64 GB, 128 GB, 256 GB, or more of high-bandwidth memory to accommodate three-dimensional CT volumes, multi-sequence MRI datasets, whole-slide pathology images, and genomic data. In some embodiments, main memory 708 may utilize error-correcting code (ECC) memory to ensure data integrity during critical medical analysis operations.

Main memory 708 may store the shared-state memory object that may maintain tensors, metadata fields, provenance identifiers, timestamps, and uncertainty values across all specialized agents. This shared-state architecture may enable seamless data flow between agents while maintaining complete audit trails for regulatory compliance. The memory structure may be organized using JSON, protobuf, or tensor-based composite data types to facilitate efficient agent communication and data serialization. Main memory 708 may also cache frequently accessed medical knowledge databases, clinical guidelines, and risk scoring models to minimize latency during real-time analysis.

In embodiments supporting federated learning, main memory 708 may temporarily store encrypted model parameters and gradient updates from multiple healthcare institutions without exposing raw patient data. The memory subsystem may implement secure memory allocation techniques to ensure patient privacy and HIPAA compliance throughout the multi-agent workflow.

User input/output interface(s) 702 may provide mechanisms for healthcare professionals to interact with the multi-agent medical imaging analysis system. These interfaces may include keyboard interfaces, mouse interfaces, touchscreen interfaces, voice recognition interfaces, gesture recognition interfaces, or specialized medical input devices. User input/output interface(s) 702 may support multiple concurrent user sessions, enabling radiologists, neurologists, pathologists, and other specialists to simultaneously review cases, annotate findings, and collaborate on diagnostic decisions.

The interfaces may provide real-time visualization of segmentation masks, attention-based overlays, Grad-CAM heatmaps, and three-dimensional reconstructions generated by the explainability agent. Healthcare professionals may use these interfaces to validate AI-generated findings, adjust confidence thresholds, modify workflow rules, or trigger manual escalation of critical cases. In embodiments supporting the collaboration agent, user input/output interface(s) 702 may enable synchronized multi-user annotation, discussion logging, and decision tracking across distributed healthcare teams.

User input/output device(s) 703 may include displays, keyboards, mice, touchscreens, medical-grade monitors, virtual reality headsets, augmented reality devices, or other peripherals connected to user input/output interface(s) 702. These devices may be specifically configured for medical imaging applications, including high-resolution diagnostic monitors with DICOM calibration, pressure-sensitive styluses for pathology annotation, or haptic feedback devices for three-dimensional anatomical exploration.

User input/output device(s) 703 may display clinical decision-support outputs generated by the multi-agent system, which may include structured summaries, segmentation visualizations, risk score outputs, explainability information, clinical trial recommendations, and drug-response predictions. The devices may support multiple display configurations to accommodate different clinical workflows, such as dual-monitor setups for comparing original images with AI-generated overlays, or large-format displays for multidisciplinary team meetings.

In embodiments supporting mobile healthcare applications, user input/output device(s) 703 may include tablets, smartphones, or wearable devices that may enable remote access to the multi-agent analysis system. These devices may receive clinical alerts generated by the escalation agent and display tiered triage designations (urgent, semi-urgent, or routine) to ensure appropriate clinical response times.

Secondary memory 710 may provide persistent storage for medical imaging data, trained neural network models, clinical databases, and system logs. Secondary memory 710 may include hard disk drive 712, removable storage drive 714, interface 620, and connections to removable storage units 718 and 622. This storage infrastructure may be designed to handle the substantial data requirements of modern medical AI systems, which may include terabytes of imaging data, multiple versions of neural network models, and comprehensive audit trails.

Hard disk drive 712 may be a high-capacity, high-performance storage device configured for medical data archival and retrieval. In some embodiments, hard disk drive 712 may be implemented using solid-state drives (SSDs), NVMe storage, or hybrid storage arrays optimized for the sequential and random-access patterns typical of medical imaging workloads. The storage system may implement RAID configurations to ensure data redundancy and availability for critical medical applications.

Hard disk drive 712 may store the complete repository of trained neural network models used by the inference agent, which may include U-Net architectures, three-dimensional convolutional neural networks, transformer models, and hybrid architectures for different medical imaging modalities. The storage system may maintain multiple model versions to support A/B testing, regression analysis, and gradual deployment of updated algorithms. In embodiments supporting the simulation agent, hard disk drive 712 may store historical labeled datasets used for evaluating the performance of updated models against ground-truth results.

Removable storage drive 714 and removable storage units 718 and 722 may provide additional storage capacity and data portability for the medical imaging analysis system. These components may include USB drives, external hard drives, optical storage devices, or specialized medical data storage appliances. Removable storage may be used for secure data transfer between healthcare institutions, backup and disaster recovery operations, or offline storage of sensitive patient data in compliance with healthcare regulations.

Interface 720 may provide connectivity between secondary memory 710 and removable storage units, supporting various storage protocols such as SATA, SAS, USB, Thunderbolt, or Fibre Channel. The interface may implement encryption and access control mechanisms to ensure that sensitive medical data remains protected during storage and transfer operations.

In embodiments supporting distributed healthcare networks, secondary memory 710 may implement cloud storage integration, enabling secure access to medical imaging data and AI models across multiple healthcare facilities. The storage system may support FHIR-compliant data formats and HL7-based communication protocols to ensure interoperability with existing hospital information systems.

Communications interface 724 may enable computer system 700 to communicate with remote devices, networks, and healthcare systems through communications path 726. This interface may support various networking technologies, which may include Ethernet, Wi-Fi, cellular networks, satellite communications, or dedicated healthcare networks. Communications interface 724 may implement advanced security protocols, which may include end-to-end encryption, certificate-based authentication, and network segmentation to protect patient data during transmission.

Remote device(s), network(s), and entity(ies) 728 may include hospital information systems, picture archiving and communication systems (PACS), electronic health record (EHR) systems, laboratory information systems, genomic databases, clinical trial registries, or other healthcare IT infrastructure. Communications interface 724 may facilitate real-time integration with these systems to retrieve patient metadata, laboratory results, prior imaging studies, and clinical history required by the clinical context agent.

In embodiments supporting telemedicine applications, communications interface 724 may enable remote access to the multi-agent medical imaging analysis system from distributed healthcare facilities, enabling specialist consultation and collaborative diagnosis across geographic boundaries. The interface may support high-bandwidth data transfer required for transmitting large medical imaging datasets and real-time streaming of diagnostic sessions.

Communications path 726 may represent various network topologies and protocols, which may include local area networks (LANs), wide area networks (WANs), virtual private networks (VPNs), or dedicated healthcare networks such as those compliant with HIPAA security requirements. The communication infrastructure may implement quality of service (QoS) mechanisms to prioritize critical medical data transmission and ensure reliable delivery of clinical alerts generated by the escalation agent.

In some embodiments, computer system 700 may be deployed in cloud computing environments, enabling scalable and cost-effective deployment of the multi-agent medical imaging analysis system. Cloud deployment may support elastic resource allocation, automatically scaling computational resources based on imaging workload demands and enabling healthcare institutions to access advanced AI capabilities without substantial infrastructure investments.

Computer system 700 may implement comprehensive security measures throughout all components, which may include hardware security modules, trusted platform modules, secure boot processes, and runtime attestation mechanisms. These security features may ensure the integrity of neural network models, protect patient data throughout the analysis pipeline, and maintain compliance with healthcare regulations such as HIPAA, GDPR, and FDA requirements for medical AI systems.

In alternative embodiments, computer system 700 may be implemented as a distributed system spanning multiple physical locations, with different specialized agents executing on optimized hardware configurations. For example, the inference agent may execute on GPU-accelerated servers, while the bias detection agent may run on CPU-optimized systems with large memory configurations. This distributed approach may enable healthcare institutions to optimize resource utilization and implement redundancy for critical medical AI operations.

The system architecture may also support edge computing deployments, where computer system 700 may be deployed directly within medical imaging equipment or mobile diagnostic units. Edge deployment may reduce latency for time-critical applications such as stroke detection or emergency triage, while maintaining connectivity to centralized resources for comprehensive analysis and reporting.

Computer system 700 may implement advanced monitoring and logging capabilities to track system performance, agent execution times, resource utilization, and diagnostic accuracy metrics. These monitoring systems may support the self-healing agent by detecting component failures, performance degradation, or anomalous behavior patterns that could indicate system malfunctions or security threats.

The hardware and software architecture of computer system 700 may be designed to support continuous operation in healthcare environments, with redundant power supplies, error-correcting memory, and automatic failover mechanisms to ensure that critical medical AI services may remain available during hardware maintenance or unexpected failures.

According to embodiments and as explained throughout, the multi-agent architecture described herein is not limited to aneurysm or stroke analysis and may be applied to any diagnostic, operational, or research workflow that requires coordinated processing of heterogeneous medical or non-medical data. Because the invention employs a unified intake→preprocessing→inference→omni-agent orchestration→downstream-agent sequence, the same framework can be extended to a wide range of imaging modalities, including oncology detection and treatment-response monitoring, cardiology imaging analysis, emergency triage for stroke, tumor, or vascular malformations, musculoskeletal injury assessment, and pulmonology screening.

In additional embodiments, the platform may support non-imaging medical domains such as digital pathology, dermatology, ophthalmology, ultrasound automation, clinical laboratory interpretation, and multimodal decision integration combining imaging, genomic, and EHR-derived features. In certain embodiments, the disclosed architecture may be further adapted for hospital-operations use cases, including radiology workflow automation, federated multi-hospital model deployment, clinical-governance tracking, real-time ICU deterioration prediction, scheduling optimization, billing-and-claims processing, and risk-adjusted coding.

In yet other embodiments, the same agent-based orchestration model may extend to pharmaceutical research, including clinical-trial matching based on multimodal biomarkers, drug-response prediction using imaging and population-level datasets, and automated biomarker discovery through coordinated radiomic, genomic, and phenotypic analysis. Because the omni-agent provides a generalized routing and decision-coordination layer, the architecture may also be commercialized as a developer platform capable of hosting third-party inference models, downstream analytic agents, custom integrations, and white-label clinical AI systems.

Moreover, the techniques described herein are applicable to non-medical imaging and industrial domains, including manufacturing defect detection, aerospace structural-health monitoring, agricultural crop-health analysis, and any scenario requiring explainable classification, risk assessment, real-time escalation, or multi-model consensus evaluation. Accordingly, the disclosed invention provides a flexible, domain-agnostic orchestration engine that enables a broad family of additional embodiments without architectural modification, allowing the same platform to support diverse clinical, operational, research, and commercial applications.

What is claimed is:

1. A computer-implemented method for orchestrated medical-imaging analysis, comprising:

receiving, by a scan intake component executed by one or more processors, medical imaging data;

preprocessing the medical imaging data to generate preprocessed data;

performing inference on the preprocessed data using one or more machine-learning models to generate inference outputs, wherein the inference outputs include one or more attribution tensors;

updating a shared-state memory object to store the inference outputs and associated metadata;

selecting, by an orchestration agent, one or more specialized agents from a plurality of specialized agents based on workflow-graph logic and one or more confidence values associated with the inference outputs stored in the shared-state memory object, wherein the one or more specialized agents includes an explainability agent;

executing the one or more selected specialized agents to generate one or more corresponding agent outputs, the executing comprising:

updating the shared-state memory object to store the one or more agent outputs including one or more explainability-related artifacts generated by the explainability agent; and continuing, by the orchestration agent, execution of the one or more selected specialized agents based on the one or more agent outputs stored in the shared-state memory object and the workflow-graph logic, and generating a clinical result based on the one or more agent outputs.

2. The method of claim 1, wherein preprocessing comprises at least one of voxel normalization, noise reduction, resampling, or orientation alignment.

3. The method of claim 1, wherein performing inference comprises generating segmentation masks, probability volumes, or bounding regions.

4. The method of claim 1, wherein the orchestration agent selects the specialized agents based on a confidence distribution, uncertainty score, or metadata completeness indicator.

5. The method of claim 1, wherein the explainability agent is configured to generate an attention-based visual overlay or a natural-language explanation.

6. The method of claim 1, wherein executing the specialized agents comprises invoking a bias-detection agent configured to compute scanner-based or demographic-based fairness metrics.

7. The method of claim 1, wherein the orchestration agent re-invokes inference using an alternative neural-network model responsive to a low-confidence inference result.

8. The method of claim 1, wherein the shared-state memory object comprises tensors, timestamps, provenance identifiers, or workflow-state indicators.

9. A medical-imaging analysis system comprising one or more processors and memory storing instructions that, when executed, cause the system to:

receive medical imaging data in a scan intake agent;

preprocess the imaging data in a preprocessing agent;

perform inference using a trained neural-network model to generate inference outputs, wherein the inference outputs include one or more attribution tensors;

store the inference outputs in a shared-state memory object;

select, by an orchestration agent, one or more specialized agents from a plurality of specialized agents based on workflow-graph routing logic and confidence values associated with the inference outputs stored in the shared-state memory object, wherein the one or more specialized agents includes an explainability agent;

execute the selected specialized agents, wherein the execution of the selected specialized agents comprises:

storing one or more agent outputs of the selected specialized agents in the shared-state memory object, wherein the one or more agents outputs include one or more explainability-related artifacts generated by the explainability agent; and continuing, by the orchestration agent, execution of the selected specialized agents based on the one or more agent outputs stored in the shared-state memory object and the workflow-graph logic; and generate a clinical output based on outputs of the selected specialized agents.

10. The system of claim 9, wherein the plurality of specialized agents comprises modular components accessible via inter-process communication or application-programming interfaces.

11. The system of claim 9, wherein the orchestration agent executes the selected specialized agents sequentially or in parallel according to workflow-graph conditions.

12. The system of claim 9, further comprising a bias-detection agent configured to compute fairness metrics using demographic-stratified error analysis.

13. The system of claim 9, wherein the explainability agent is configured to generate heatmap-based visualizations.

14. The system of claim 9, wherein the orchestration agent invokes a fallback inference model having a distinct architecture or training dataset.

15. The system of claim 9, wherein the workflow-graph comprises nodes corresponding to individual agents and edges specifying routing conditions.

16. A non-transitory computer-readable medium storing instructions that, when executed by one or more processors, cause the processors to:

receive medical imaging data;

perform preprocessing to generate normalized imaging data;

apply machine-learning inference to generate inference outputs, wherein the inference outputs include one or more attribution tensors;

update a shared workflow state to store the inference outputs and metadata values;

invoke, using an orchestration agent, one or more specialized agents selected according to workflow-graph rules and confidence values associated with the inference outputs stored in the shared-state memory object, wherein the one or more specialized agents includes an explainability agent, the invocation comprising:

storing one or more agent outputs of the one or more specialized agents in the shared-state memory object, wherein the one or more agent outputs includes one or more explainability-related artifacts generated by the explainability agent; and continuing, by the orchestration agent, execution of the one or more specialized agents based on the one or more agent outputs stored in the shared-state memory object and the workflow-graph logic; and generate a structured clinical result based on outputs of the specialized agents.

17. The non-transitory computer-readable medium of claim 16, wherein the instructions further cause the processors to compute quality metrics comprising at least a signal-to-noise ratio, slice-continuity score, or artifact-presence score.

18. The non-transitory computer-readable medium of claim 16, wherein the specialized agents comprise at least the explainability agent, a clinical-context agent, or a risk-scoring agent.

19. The non-transitory computer-readable medium of claim 16, wherein the instructions further cause the processors to validate consistency between segmentation outputs and natural-language explanations.

20. The non-transitory computer-readable medium of claim 16, wherein generating the structured clinical result comprises aggregating outputs from at least three specialized agents.

* * * * *